(12) United States Patent
Banno et al.

(10) Patent No.: US 10,503,987 B2
(45) Date of Patent: Dec. 10, 2019

(54) APPARATUS DETECTING DRIVING INCAPABILITY STATE OF DRIVER

(71) Applicant: DENSO CORPORATION, Kariya, Aichi-pref. (JP)

(72) Inventors: Hiroto Banno, Kariya (JP); Yutaka Munaoka, Kariya (JP); Takuhiro Omi, Kariya (JP); Takeshi Enya, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 155 days.

(21) Appl. No.: 15/320,945

(22) PCT Filed: Jun. 8, 2015

(86) PCT No.: PCT/JP2015/002863
§ 371 (c)(1),
(2) Date: Dec. 21, 2016

(87) PCT Pub. No.: WO2015/198540
PCT Pub. Date: Dec. 30, 2015

(65) Prior Publication Data
US 2017/0161575 A1    Jun. 8, 2017

(30) Foreign Application Priority Data

Jun. 23, 2014  (JP) ................. 2014-128386
Jun. 23, 2014  (JP) ................. 2014-128388

(51) Int. Cl.
*G06K 9/00* (2006.01)
*B60K 28/06* (2006.01)
(Continued)

(52) U.S. Cl.
CPC ........ *G06K 9/00845* (2013.01); *A61B 5/0077* (2013.01); *A61B 5/1103* (2013.01);
(Continued)

(58) Field of Classification Search
CPC ............ A61B 2503/22; A61B 2576/02; A61B 5/0077; A61B 5/1103; A61B 5/1116;
(Continued)

(56) References Cited

U.S. PATENT DOCUMENTS

| 4,625,329 A | 11/1986 | Ishikawa et al. |
| 5,008,946 A | 4/1991 | Ando |

(Continued)

FOREIGN PATENT DOCUMENTS

| CN | 103434400 A | 12/2013 |
| JP | H0757172 A | 3/1995 |

(Continued)

OTHER PUBLICATIONS

U.S. Appl. No. 15/321,048, filed Dec. 21, 2016, Hiroto Banno.
U.S. Appl. No. 15/321,004, filed Dec. 21, 2016, Hiroto Banno.
U.S. Appl. No. 16/145,282, filed Sep. 28, 2018, Hiroto Banno.

*Primary Examiner* — Farzana Hossain
(74) *Attorney, Agent, or Firm* — Harness, Dickey & Pierce, P.L.C.

(57) ABSTRACT

An apparatus detecting driving incapability state of a driver includes: an inclination detection portion that detects inclination of a head of a driver with respect to a trunk of the driver lower than a neck, based on an image of a driver seat captured by an imaging device mounted on a vehicle; and a posture collapse detection portion that detects the driver is incapable of driving when the inclination of the head detected by the inclination detection portion is greater than a relative inclination threshold during travel of the vehicle.

30 Claims, 13 Drawing Sheets

(51) Int. Cl.
  *B60W 40/02* (2006.01)
  *B60W 40/08* (2012.01)
  *B60W 40/10* (2012.01)
  *G08G 1/0962* (2006.01)
  *A61B 5/00* (2006.01)
  *A61B 5/11* (2006.01)
  *A61B 5/18* (2006.01)
  *G08G 1/16* (2006.01)
  *B60K 35/00* (2006.01)
  *G01S 19/13* (2010.01)

(52) U.S. Cl.
  CPC .............. *A61B 5/1121* (2013.01); *A61B 5/18* (2013.01); *A61B 5/6893* (2013.01); *B60K 28/06* (2013.01); *B60W 40/02* (2013.01); *B60W 40/08* (2013.01); *B60W 40/10* (2013.01); *G06K 9/00228* (2013.01); *G06K 9/00342* (2013.01); *G08G 1/0962* (2013.01); *A61B 5/1116* (2013.01); *A61B 2503/22* (2013.01); *A61B 2576/02* (2013.01); *B60K 35/00* (2013.01); *B60K 2370/1438* (2019.05); *B60K 2370/152* (2019.05); *B60K 2370/21* (2019.05); *G01S 19/13* (2013.01); *G08G 1/16* (2013.01)

(58) Field of Classification Search
  CPC ....... A61B 5/1121; A61B 5/18; A61B 5/6893; B60K 2350/1028; B60K 2350/106; B60K 2350/2013; B60K 28/06; B60K 35/00; B60W 40/02; B60W 40/08; B60W 40/10; G01S 19/13; G06K 9/00228; G06K 9/00342; G06K 9/00845; G08G 1/0962; G08G 1/16
  USPC .................................................. 348/77, 148
  See application file for complete search history.

(56) References Cited

U.S. PATENT DOCUMENTS

| | | | |
|---|---|---|---|
| 5,353,013 | A | 10/1994 | Estrada |
| 6,049,747 | A | 4/2000 | Nakajima et al. |
| 6,304,187 | B1 | 10/2001 | Pirim |
| 6,550,686 | B2 | 4/2003 | Kawai et al. |
| 6,717,518 | B1 | 4/2004 | Pirim et al. |
| 6,915,231 | B2 | 7/2005 | Kim |
| 6,927,694 | B1 | 8/2005 | Smith et al. |
| 7,333,006 | B2 | 2/2008 | Ogawa |
| 7,460,940 | B2 | 12/2008 | Larsson et al. |
| 7,466,847 | B2 | 12/2008 | Komura |
| 7,821,382 | B2 | 10/2010 | Kameyama |
| 7,859,652 | B2 | 12/2010 | Uechi |
| 7,860,280 | B2 | 12/2010 | Danowitz |
| 8,050,453 | B2 | 11/2011 | Yang et al. |
| 8,094,883 | B2 | 1/2012 | Nagai et al. |
| 8,208,027 | B2 | 6/2012 | Shimura |
| 8,356,899 | B2 | 1/2013 | Hirata |
| 8,487,775 | B2 | 7/2013 | Victor et al. |
| 8,538,072 | B2 | 9/2013 | Kelly et al. |
| 8,542,910 | B2 | 9/2013 | Leyvand et al. |
| 8,599,266 | B2 | 12/2013 | Trivedi et al. |
| 8,604,932 | B2 | 12/2013 | Breed et al. |
| 9,041,543 | B2 | 5/2015 | Inada |
| 9,274,597 | B1 | 3/2016 | Karakotsios et al. |
| 9,330,305 | B2 | 5/2016 | Zhao et al. |
| 9,721,173 | B2 | 8/2017 | Xu et al. |
| 9,963,153 | B2 | 5/2018 | An et al. |
| 2001/0039806 | A1 | 11/2001 | Kawai et al. |
| 2003/0079929 | A1 | 5/2003 | Takagi et al. |
| 2003/0128123 | A1* | 7/2003 | Sumiya ................ G08B 23/00 340/573.1 |
| 2005/0180605 | A1 | 8/2005 | Toyama |
| 2006/0187305 | A1 | 8/2006 | Trivedi et al. |
| 2006/0235615 | A1 | 10/2006 | Kato et al. |
| 2007/0183651 | A1 | 8/2007 | Comaniciu et al. |
| 2008/0204239 | A1 | 8/2008 | Marszalek et al. |
| 2008/0267460 | A1 | 10/2008 | Aoki et al. |
| 2010/0014711 | A1 | 1/2010 | Camhi et al. |
| 2010/0214105 | A1 | 8/2010 | Manotas, Jr. |
| 2013/0073115 | A1 | 3/2013 | Levin et al. |
| 2013/0147936 | A1 | 6/2013 | Lee et al. |
| 2013/0207805 | A1 | 8/2013 | Inada |
| 2013/0257620 | A1* | 10/2013 | Tsou ...................... A61B 5/18 340/573.1 |
| 2014/0019167 | A1* | 1/2014 | Cheng ................... G06Q 40/08 705/4 |
| 2014/0121927 | A1 | 5/2014 | Hanita |
| 2015/0009010 | A1* | 1/2015 | Biemer ................ G06F 21/32 340/5.83 |
| 2015/0109429 | A1* | 4/2015 | Inoue ...................... A61B 5/18 348/78 |
| 2015/0186715 | A1 | 7/2015 | Zhao et al. |
| 2015/0186737 | A1 | 7/2015 | Omi et al. |
| 2015/0266484 | A1 | 9/2015 | Moran et al. |
| 2015/0379362 | A1* | 12/2015 | Calmes ................ G06K 9/2036 348/136 |
| 2017/0001648 | A1 | 1/2017 | An et al. |
| 2017/0140232 | A1* | 5/2017 | Banno ...................... G06T 7/70 |
| 2017/0143253 | A1 | 5/2017 | Krenzer et al. |
| 2017/0161575 | A1 | 6/2017 | Banno et al. |
| 2017/0287139 | A1 | 10/2017 | Lee et al. |
| 2019/0034744 | A1 | 1/2019 | Banno et al. |

FOREIGN PATENT DOCUMENTS

| | | |
|---|---|---|
| JP | H08216728 A | 8/1996 |
| JP | H10000960 A | 1/1998 |
| JP | 2000130205 A | 5/2000 |
| JP | 2004314750 A | 11/2004 |
| JP | 2006318446 A | 11/2006 |
| JP | 3943367 B2 | 7/2007 |
| JP | 2007249477 A | 9/2007 |
| JP | 2009289136 A | 12/2009 |
| JP | 2012254745 A | 12/2012 |
| JP | 2013054744 A | 3/2013 |
| JP | 2014019301 A | 2/2014 |
| WO | WO-2013/008300 A1 | 1/2013 |

* cited by examiner

NORMAL DRIVING

SUDDEN ILLNESS ONSET
POSTURE COLLAPSE (WITHIN FA)

POSTURE COLLAPSE (OUTSIDE FA)

MOTION OF PICKING OBJECT UP

NORMAL DRIVING

SUDDEN ILLNESS ONSET
POSTURE COLLAPSE (WITHIN FA)

INATTENTION

MOTION OF PICKING OBJECT UP

APPARATUS DETECTING DRIVING INCAPABILITY STATE OF DRIVER

CROSS REFERENCE TO RELATED APPLICATIONS

This application is a U.S. National Phase Application under 35 U.S.C. 371 of International Application No. PCT/JP2015/002863 filed on Jun. 8, 2015 and published in Japanese as WO 2015/198540 A1 on Dec. 30, 2015. This application is based on and claims the benefit of priority from Japanese Patent Application No. 2014-128386 filed on Jun. 23, 2014 and Japanese Patent Application No. 2014-128388 filed on Jun. 23, 2014. The entire disclosures of all of the above applications are incorporated herein by reference.

TECHNICAL FIELD

The present disclosure relates to apparatus detecting driving incapability state of a driver, the apparatus detecting a situation in which a driver has become unable to drive.

BACKGROUND ART

Heretofore, in the event that a driver becomes unable to drive due to a sudden illness or the like during his or her driving a vehicle, an accident may be caused. Therefore, to prevent accidents by detecting such driving incapability state of a driver has been proposed.

A drive control apparatus described in Patent Literature 1 detects pressing force of buttocks on the seat portion of a driver seat, pressing force of back on a seat back, and pressing force of left foot on a floor, and on the basis of the pressing forces distribution, the drive control apparatus determines whether the driver's posture is a normal posture, forward inclining posture, or backward inclining posture. When the driver's posture is a forward or backward inclining posture, the drive control apparatus determines that something wrong with driver's physical condition.

In an emergency refuge-seeking apparatus described in Patent Literature 2, various information is acquired from, for example, a sight line or face direction measurement device, thereby recognizing the driver's condition, such as degree of deterioration of driver's consciousness, degree of driver's awakeness, or driver's posture. When a driver's state declines, emergency refuge-seeking assistance is provided. The sight line or face direction measurement device captures an image of a driver by means of a driver camera and recognizes items of information about, for example, driver's sight line, blinking, and face direction from the captured image.

The inventors of the present application have found the following. Not only when the driver's posture inclines forward or backward due to his or her having a sudden illness or the like, but also when the driver picks up an object on a front passenger seat during driving, the driver's posture may collapsed, resulting in similar pressing forces distribution as in the case of sudden illness. In the apparatus described in Patent Literature 1, posture collapse, caused by factors other than driver's seizure or the like, are not taken into account. Therefore, the device may erroneously detect driver's driving incapability.

In addition, the inventors of the present application have found the following. In the event that a driver has a sudden illness or the like during his or her driving, direction of the driver's face may collapse. However, direction of the driver's face may collapse also when the driver drives looks aside during driving, for example. In the apparatus described in the Patent Literature 2, collapse direction of a face, caused by factors other than deterioration of driver's consciousness, sudden illness, or the like, are not taken into account. Therefore, the device may erroneously detect driving incapability state of a driver.

PRIOR ART LITERATURE

Patent Literature

Patent Literature 1: JP 2012-254745 A
Patent Literature 2: JP 2014-19301 A

SUMMARY OF INVENTION

The present disclosure has been made in view of such a drawback and it is an object of the present disclosure to provide apparatus detecting driving incapability state of a driver, the apparatus being able to detect with high accuracy a situation in which the driver has become unable to drive.

According to one aspect of the present disclosure, apparatus detecting driving incapability state of a driver includes: an inclination detection portion that detects inclination of a head of a driver with respect to a trunk of the driver lower than a neck, based on an image of a driver seat captured by an imaging device mounted on a vehicle; and a posture collapse detection portion that detects the driver is incapable of driving when the inclination of the head detected by the inclination detection portion is greater than a relative inclination threshold during travel of the vehicle.

According to the apparatus detecting driving incapability state of a driver, an inclination of the head with respect to the trunk part of the driver is detected on the basis of a captured image of a driver seat. In general, the trunk of the driver is restrained by the seat and seat belt of the driver seat. Therefore, even when the driver has become unconscious, the trunk is less likely to move. By contrast, since the head of the driver is not usually restrained, the driver has to keep the head in position by voluntary effort. Therefore, when the driver becomes unconscious due to a sudden illness, the driver cannot keep the head in position, and the head may significantly incline in some direction with respect to the trunk.

On the other hand, when the driver picks up an object located away from the driver seat, the driver generally inclines the trunk consciously. Therefore, the inclination of the head to the trunk is usually small. When a driver looks aside during driving, the driver generally sees by turning his or her head, and therefore the inclination of the head to the trunk is usually small.

Thus, when the inclination of the head with respect to the trunk is greater than a relative inclination threshold, there is a high possibility of posture collapse resulting from having a sudden illness rather than from picking up an object. Accordingly, when the inclination of the head with respect to the trunk is greater than the relative inclination threshold, the driving incapability state of the driver is detected, and it is possible to detect the driving incapability state of the driver with high accuracy.

BRIEF DESCRIPTION OF DRAWINGS

The above and other aspects, features and advantages of the present disclosure will become more apparent from the following detailed description made with reference to the accompanying drawings. In the drawings.

DESCRIPTION OF EMBODIMENTS

An embodiment of apparatus detecting driving incapability state of a driver will be described below with reference to the drawings. It is noted that, in the present embodiment, the driving incapability state of a driver includes a state of a driver being unable to drive a vehicle due to loss of driver's consciousness resulting from his or her having had a sudden illness, and a state of a driver unable to drive a vehicle since, though the driver is conscious, the driver cannot move his or her body resulting from his or her having had a sudden illness such as a heart attack.

Figure 1:
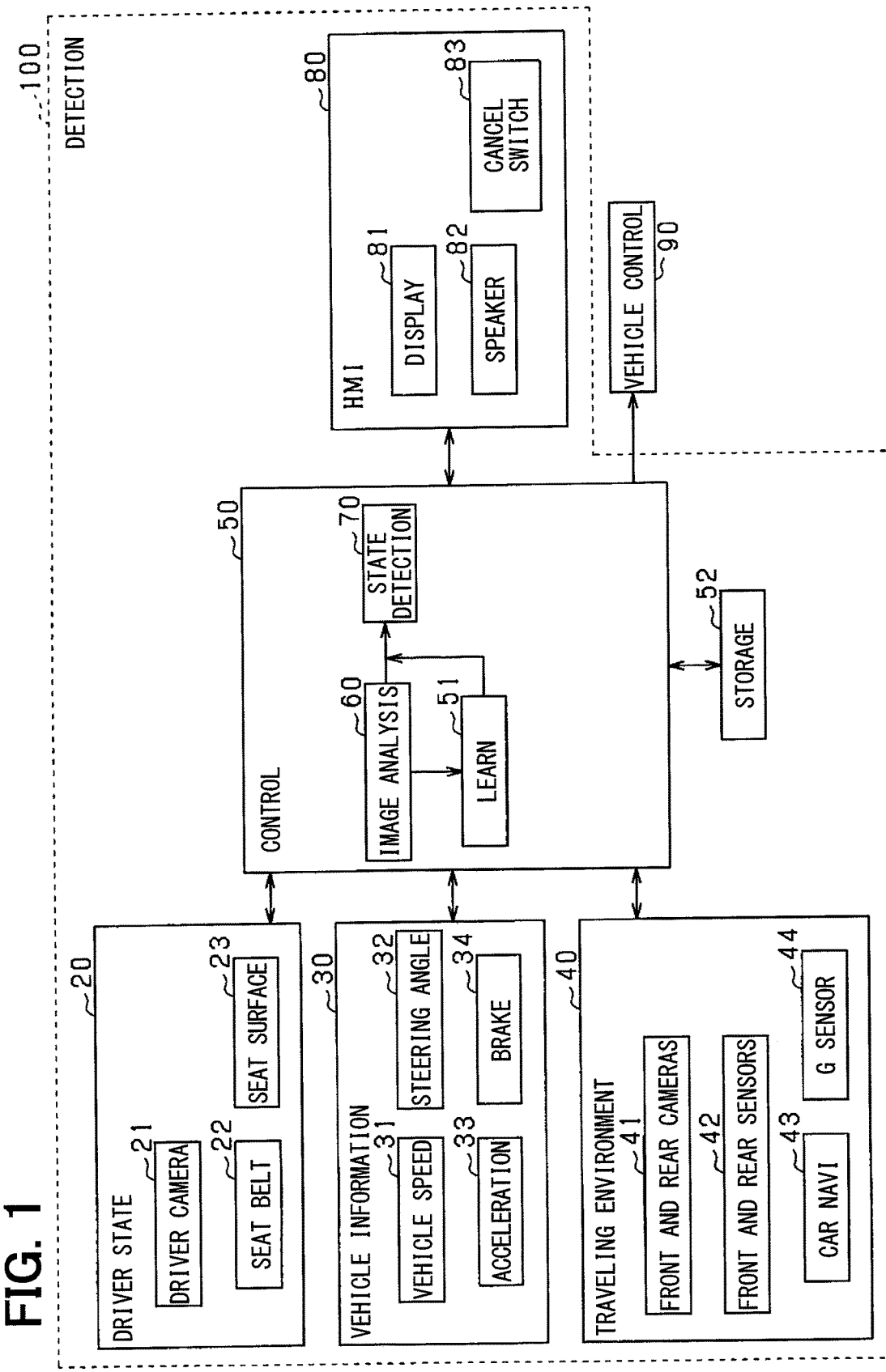
FIG. 1 is a block diagram illustrating a configuration of apparatus detecting driving incapability state of a driver.
Figure 2:
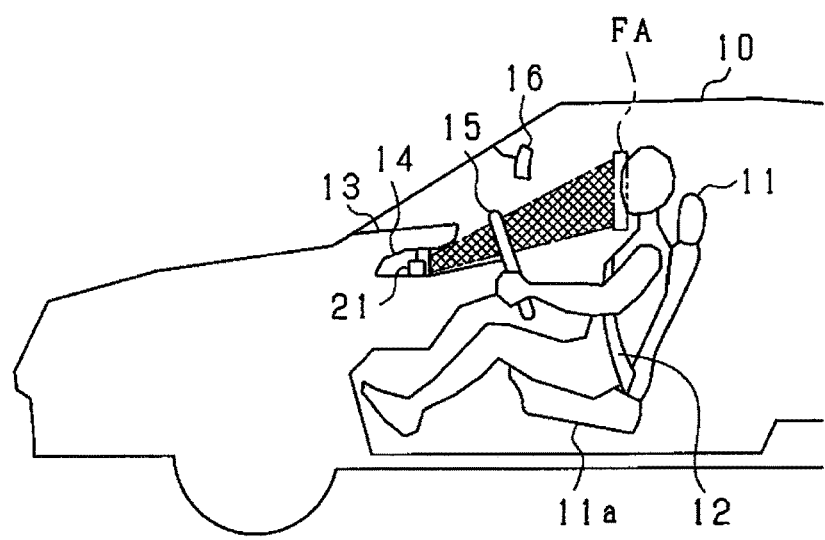
FIG. 2 is a diagram showing a vehicle cabin on which the apparatus detecting driving incapability state of a driver is mounted.
Figure 3:
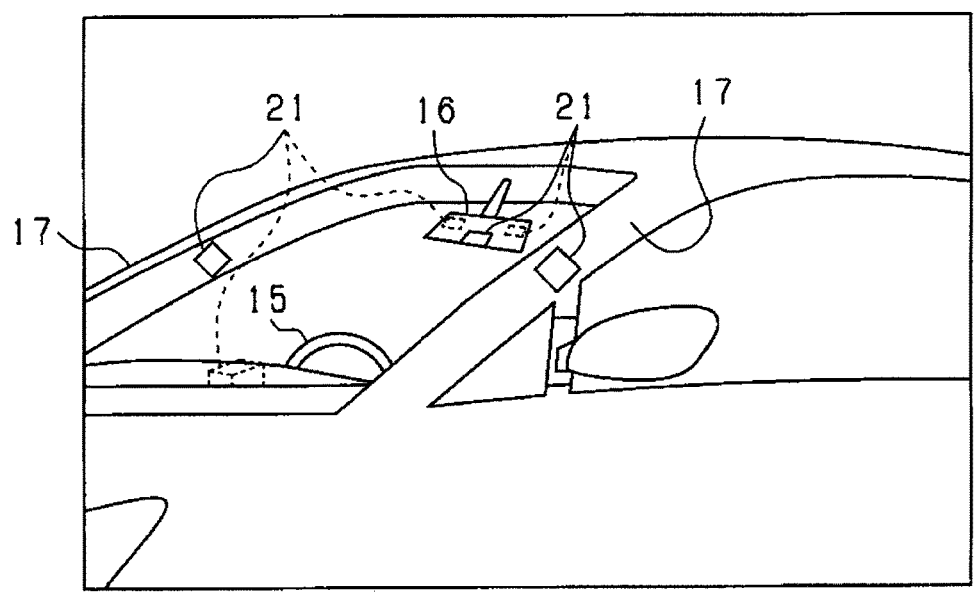
FIG. 3 is a diagram showing the driver seat of a vehicle on which the apparatus detecting driving incapability state of a driver is mounted.

First, the configuration of detection apparatus 100 (apparatus detecting driving incapability state of a driver) according to the present embodiment will be described with reference to FIGS. 1 to 3. The detection apparatus 100 includes a controller 50, a driver state recognition device 20, a vehicle information recognition device 30, a traveling environment recognition device 40, a HMI (Human Machine Interface) 80, and a storage device 52. The detection apparatus 100 detects a driving incapability state of a driver. When the detection apparatus 100 asks a driver that the driver is unable to drive and does not receive a response from the driver, the detection apparatus 100 transmits to a vehicle controller 90 a command to safely stop the vehicle.

The driver state recognition device 20 includes multiple driver cameras 21, a seat belt sensor 22, and a seat surface sensor 23. The driver cameras 21 correspond to imaging devices. The seat belt sensor 22 corresponds to an amount detection portion. The seat surface sensor 23 corresponds to a seat pressure detection portion. The driver cameras 21 are, for example, CCD cameras and capture images of a driver seat illuminated by an illumination device such as a near infrared LED. As shown in FIGS. 2 and 3, the driver cameras 21 are respectively mounted on a meter panel 14, substantially in the middle of the lower edge of a back mirror 16, and on the right and left A pillars 17, so as to face a driver. The driver camera 21 may be installed, instead of on the meter panel 14, on a dashboard 13 (shown by broken lines) or in a steering column. The driver camera 21 may be installed on, instead of the lower edge of the back mirror 16, the left or right edge (shown by broken lines) of the back mirror 16. These four driver cameras 21 compose a driver status monitor, and capture, per second, dozens of images of the upper front body of a driver seated on a seat 11 of the driver seat.

The seat belt sensor 22 is a sensor that detects an amount by which a seat belt 12 is drawn out. Specifically, the seat belt sensor 22 is an encoder that detects the rotation angle of a motor that feeds out and takes up the seat belt 12. The seat surface sensor 23 is a sensor that detects the pressure distribution of a seat portion 11a of the seat 11 of the driver seat.

The vehicle information recognition device 30 includes a vehicle speed sensor 31, a steering angle sensor 32, an acceleration sensor 33, and a brake sensor 34. The vehicle speed sensor 31 is a sensor that detects a speed of a vehicle 10. The steering angle sensor 32 is a sensor that detects a steering angle of a steering wheel 15. The acceleration sensor 33 is a sensor that detects an opening degree of an accelerator, that is, a degree of operation of an accelerator pedal. The brake sensor 34 detects a degree of operation of a brake pedal.

The traveling environment recognition device 40 includes front and rear cameras 41, front and rear sensors 42, a car navigation device 43, and a G sensor 44. The front and rear cameras 41 include a camera that captures an image of a scene in the forward direction of the vehicle 10 as well as white lines on the road, and a camera that captures an image of a scene in the backward direction and backward sideways direction of the vehicle 10. The front and rear sensors 42 are sensors such as an ultrasonic sensor, a laser radar, or a millimeter wave radar. The front and rear sensors 42 obtain distances between the vehicle 10 and objects ahead of and behind the vehicle 10, respectively, by detecting objects ahead of and behind the vehicle 10. Based on distances between the vehicle 10 and vehicles ahead of and behind the vehicle 10, obtained by the front and rear sensors 42, speeds (a relative speed) relative to vehicles ahead of and behind the vehicle 10 can be calculated.

Using a GPS signal received by a GPS receiver and information obtained by various sensors including a G sensor, the car navigation device 43 calculates the present location of the vehicle 10, and calculates a guiding route from the present location to a destination. The G sensor 44 is installed, for example, on the seat 11 and detects accelerations in three-dimensions including front/rear, left/right, and up/down of the vehicle 10. The G sensor 44 may be a sensor that the car navigation device 43 has. Alternatively, in a case where the vehicle 10 has an advanced vehicle operation system (AVOS), the G sensor 44 may be a sensor that the AVOS has. That is, in a case where the G sensor 44 has been installed for another application, the sensor may be shared.

The controller 50 is a microcomputer including a CPU, a ROM, a RAM, an I/O, and so on. The controller 50 obtains various information from the driver state recognition device 20, the vehicle information recognition device 30, the traveling environment recognition device 40, the storage device 52, and the HMI 80. The controller 50 and the various devices are connected by wired communication such as CAN, and wireless communication such as LAN and Bluetooth (registered trademark). In the controller 50, the CPU executes various programs stored in the ROM, thereby achieving the functions of an image analysis portion 60, a learning portion 51, and a state detection portion 70, and thus detecting the driving incapability state of a driver. Detailed explanation of each portion will be described below.

The HMI 80 (corresponding to a posture notification portion and an inquiry portion) includes a display 81, a speaker 82, and a cancellation switch 83. The display 81 includes a display of the car navigation device 43 and an on-vehicle display provided in a meter panel 14. The display 81 may be a touch display having a liquid crystal panel or an organic EL panel. Based on driver's posture detected from an image, the display 81 notifies his or her degree of posture collapse. Specifically, the display 81 displays the status of a driver's posture in five stages. The highest level 5 of posture collapse is a level at which a driver has had a sudden illness and is unable to keep a driving posture, that is, the level at which it is determined as the driving incapability state. The driver can check his or her driving posture by looking at the posture status displayed on the display 81. Accordingly, when the posture collapse level approaches level 5, the driver can correct the driving posture before it is determined as the driving incapability state.

The speaker 82 is an on-vehicle speaker shared with the car navigation device 43, an audio device, and so on. When the driving incapability state of the driver is detected, the speaker 82 asks the driver by sound whether he or she is unable to drive. The display 81 may display a screen for checking the driving incapability state. The speaker 82 may notify the driver of his or her level of posture collapse by sound.

The cancellation switch 83 is a switch to stop a detection of the driving incapability state. When the cancellation switch 83 is operated once, detection of the driving incapability state is suspended for a period of one trip. Otherwise, when the cancellation switch 83 is operated during a trip, the detection of the driving incapability state is suspended during operation of the cancellation switch 83 or for a fixed time (about several seconds) after the operation. Therefore, operating the cancellation switch 83 in advance when a driver picks an object up prevents that posture collapse of the driver from being erroneously detected as driving incapability state.

Figure 4:
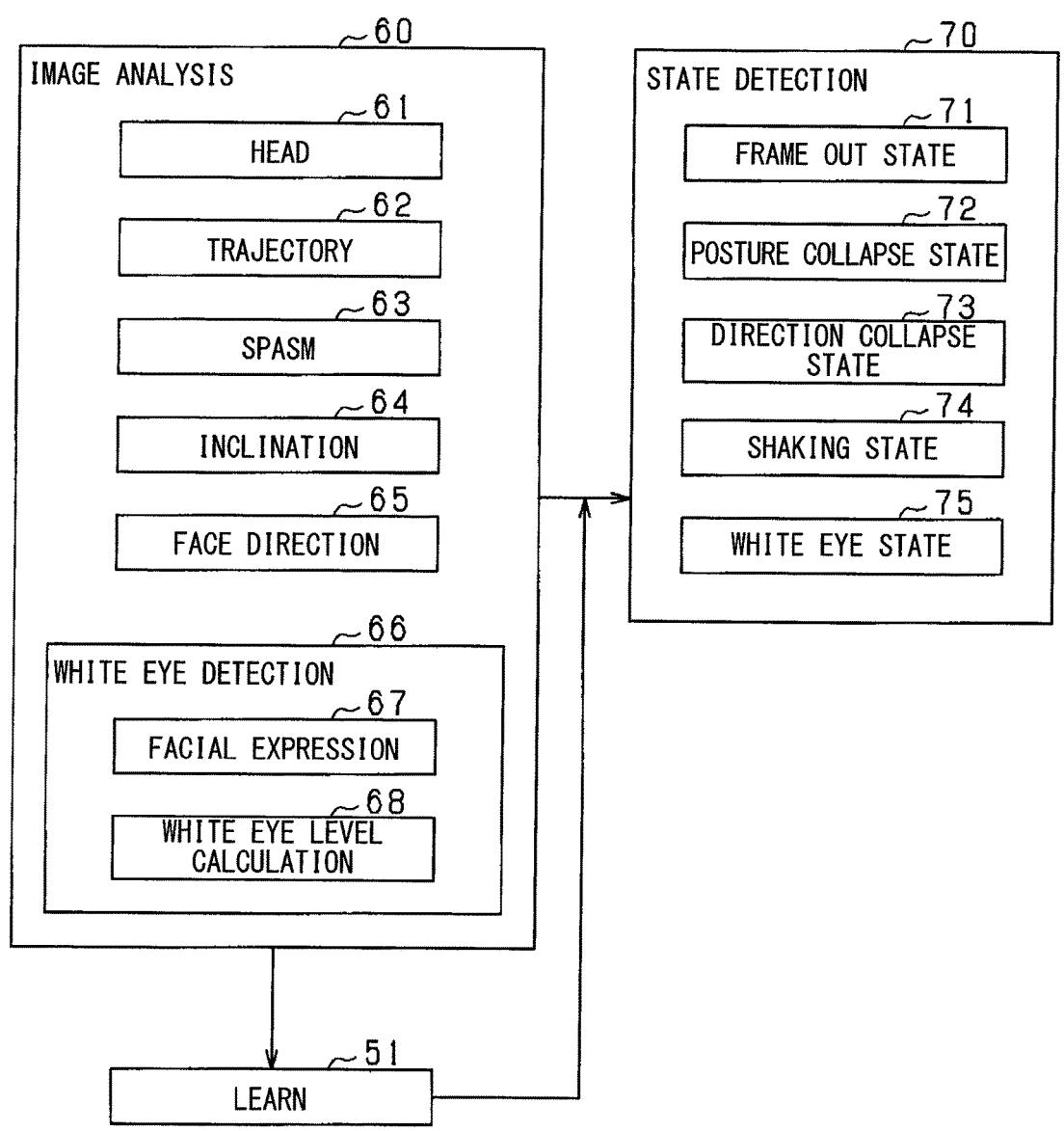
FIG. 4 is a block diagram showing functions of a controller.

Next, various functions achieved by the controller 50 will be described with reference to FIG. 4. The image analysis portion 60 includes a head detection portion 61, a trajectory acquisition portion 62, a spasm detection portion 63, an inclination detection portion 64, a face direction detection portion 65, and a white eye detection portion 66.

Based on images of the driver seat captured by the driver cameras 21, the head detection portion 61 sequentially detects the head part of a driver above his or her neck. Specifically, each time an image of the driver seat is captured by any one of the driver cameras 21, the head detection portion 61 extracts from the image of the driver seat an edge defining the outline of the head of a driver, and detects, as the driver's head, the area surrounded by the extracted edges.

The trajectory acquisition portion 62 acquires the trajectory of the head of a driver from the positions of the driver's head sequentially detected by the head detection portion 61. The trajectory acquisition portion 62 uses, as the position of the head, the center of the head of the driver detected in each image, and connects the positions of the head in the corresponding images, to acquire the trajectory of the head.

The spasm detection portion 63 detects spasm of a driver, that is, involuntary muscular contraction of the trunk part of the driver below his or her head and neck. Specifically, the spasm detection portion 63 extracts edges defining the head and the trunk of a driver from each image. When edges extracted from sequential images vibrate regularly (periodically), the spasm detection portion 63 detects that the driver has a spasm.

Based on the image of the driver seat, the inclination detection portion 64 detects the inclination θ of the head of the driver with respect to his or her trunk. Specifically, the inclination detection portion 64 detects, as a head and a trunk, areas surrounded by edges respectively defining the outlines of the head and the trunk. The inclination detection portion 64 also detects the respective center axes of the head and the trunk. The inclination detection portion 64 uses, as the inclination θ of the head, the inclination of the center axis of the head with respect to the center axis of the trunk. The pattern of the direction of the trunk, prepared in advance, and the direction of the detected trunk are compared to determine the direction of the trunk, thereby detecting the center axis of the trunk from the trunk the direction of which has been determined. Meanwhile, the features of a face included in the head, such as eyes, a nose, and a mouth, are extracted, and the center axis of the head is detected from the three-dimensional arrangement of the features of the face. When the head inclines forwards, the distances between the features of the face and the front of the vehicle become shorter; and conversely when the head inclines backward, the distances between the features of the face and the front of the vehicle become longer. To detect the center axis of the head, the distances between the features of the face in the forward and backward directions of the vehicle may be used.

Alternatively, the inclination detection portion 64 detects the seat belt 12 of the driver seat from the image of the driver seat, and detects the inclination θ of a head with respect to the trunk from the positional relation between the seat belt 12 and the head. Since the trunk of the driver is restricted by the seat belt 12, the position of the trunk can be estimated from the position of the seat belt 12.

Based on the image of the driver seat, the face direction detection portion 65 detects the direction of the face of a driver with respect to the front of the vehicle 10. The face direction detection portion 65 detects, as the direction of a face, the inclination of the face with respect to a vertical plane of the vehicle 10 opposite the front face of the vehicle 10.

The white eye detection portion 66 includes a facial expression detection portion 67 and a white eye exposure calculation portion 68, and detects a state in which the eyes of a driver have rolled back. Here, a state in which eyes are rolled back includes not only a state in which the eyes are completely rolled back, as shown in FIG. 15C, but also a state in which the black eye regions are seen less than a predetermined amount, as shown in FIG. 15B. That is, a state in which eyes are rolled back refers to a state in which the black of the eyes are deviated and field of vision is, therefore, narrower than a predetermined range.

Based on the image of the driver seat, the facial expression detection portion 67 detects the outline of each eye of a driver as well as the black eye region. The outline of each eye of the driver refers to the boundary between the eye and the eyelid. The black eye region means an area lower in color value than a white area in the area inside the outline of each eye. Therefore, the region is not limited to black but may be a colored region such as blue, brown, or gray. The facial expression detection portion 67 detects whether a driver's mouth is open, from the extracted edges defining the outline of the mouth.

The white eye exposure calculation portion 68 calculates the exposure of the white of each eye by a driver based on the outline and black eye region detected by the facial expression detection portion 67.

Figure 15A:
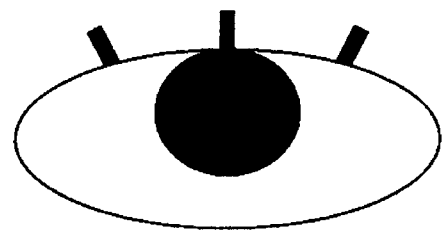
FIG. 15A is a diagram showing a normal state.
Figure 15B:
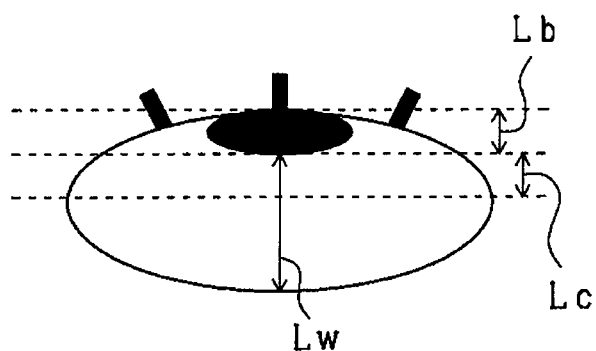
FIG. 15B is a diagram showing a state in which an eye is rolled back.
Figure 15C:
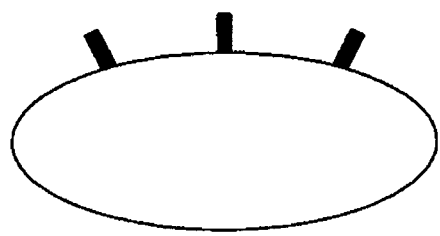
FIG. 15C is a diagram showing a state in which an eye is completely rolled back.

Specifically, the white eye exposure calculation portion 68 calculates the exposure of the white of eye from the ratio of the length (Lw+Lb) in a vertical direction of the area surrounded by the outline of the eye to the length Lb in a vertical direction of the black eye region (see FIGS. 15A to 15C). The shorter the Lb is with respect to the length (Lw+Lb), the higher the exposure of the white of eye is. Alternatively, the white eye exposure calculation portion 68 calculates the exposure of the white of eye based on a distance Lb from the top of the outline of each eye to the lowermost part of the black eye region. The shorter the distance Lb is, the higher the exposure of the white of eye is. Alternatively, the white eye exposure calculation portion 68 calculates the exposure of the white of eye based on the ratio of the area of the white eye region, obtained by removing the area of the black eye region from the area of the entire eye region surrounded by the outline of each eye, to the area of the black eye region. The smaller the area of the black eye region is with respect to the area of the white eye region, the higher the exposure of the white of eye is.

Alternatively, the white eye exposure calculation portion 68 calculates the exposure of the white of eye based on the oblateness of each black eye region. When each eye is rolled back, the black eye region is rolled upward, resulting that apparent oblateness of the black eye region becomes higher. The higher the oblateness of the black eye region is, the higher the exposure of the white of eye is. Alternatively, the white eye exposure calculation portion 68 calculates the exposure of the white of eye based on a distance Lc from the center line, which is the center in the vertical direction of the area surrounded by the outline of each eye, to the lowermost part of the black eye region.

The learning portion 51 learns the inclination θ of the head, detected by the inclination detection portion 64, when the driver is not incapable of driving. In addition, when the driver is not incapable of driving, the learning portion 51 also learns the direction of the face detected by the face direction detection portion 65. Furthermore, when the driver is not in the driving incapability state, the learning portion 51 learns the amplitudes of the shakes of the head detected by the head detection portion 61. That is, the learning portion 51 learns the habitual driving postures of the driver. When there are two or more drivers of the vehicle 10, the learning portion learns the habitual driving postures for each driver.

The state detection portion 70 includes an out-of-frame detection portion 71, a posture collapse detection portion 72, a direction collapse detection portion 73, a shake detection portion 74, and a white eye state detection portion 75.

The out-of-frame detection portion 71 determines an out of frame during travel of the vehicle 10. When the out of frame is detected, the out-of-frame detection portion 71 detects that the driver is incapable of driving. Specifically, when the head of the driver, detected by the head detection portion 61, is outside the range FA of an image, the out-of-frame detection portion 71 detects the driver is incapable of driving. Here, the range FA is a predetermined range of an image captured by each driver camera 21. During normal driving, the head of a driver does not fall outside the range FA. The range FA may be the entire image captured.

Figure 5A:
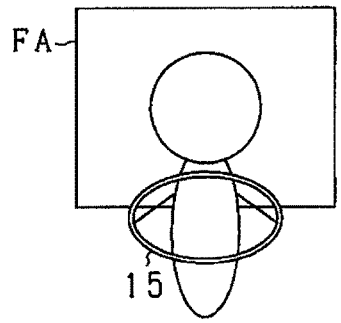
FIG. 5A is a diagram showing a posture during normal driving.
Figure 5B:
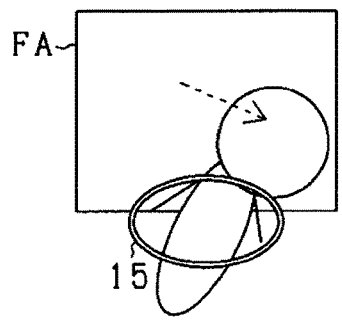
FIG. 5B is a diagram showing a posture collapse (within FA) when a driver has a sudden illness.
Figure 5C:
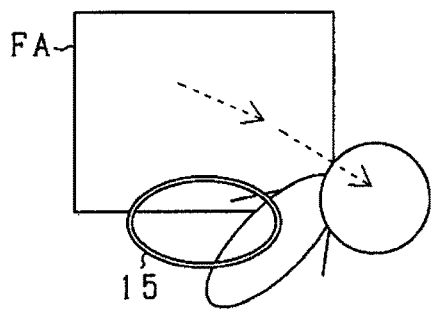
FIG. 5C is a diagram showing a posture collapse (outside FA) when the driver has a sudden illness.
Figure 6:
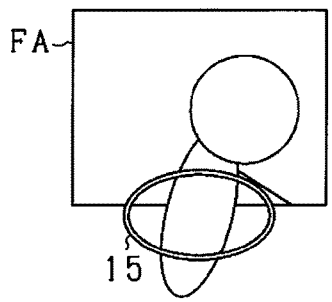
FIG. 6 is a diagram showing a posture of picking an object up.

When a driver is driving the vehicle 10 normally, the head of the driver usually falls within the range FA of an image even when he or she moves to pick an object up, as shown in FIG. 6. Compared to this, when the driver becomes unconscious due to sudden illness, the head of the driver may fall outside the range FA, as shown in FIGS. 5A to 5C. Therefore, when the head of the driver is outside the range FA of an image, the out-of-frame detection portion 71 detects that the driver is incapable of driving.

At this time, by taking account of the trajectory acquired by the trajectory acquisition portion 62 by the time the head falls out of the range FA, the out-of-frame detection portion 71 is able to improve accuracy in detecting the driving incapability state of the driver. Using the trajectory of the head makes it possible to distinguish between a case where the head of the driver cannot be detected within the range FA due to an unclear imaging or the like and a case where the head of the driver has moved and cannot be detected within the range FA. Accordingly, detection accuracy of the driving incapability state of a driver improves.

When the head becomes undetectable, for example, when the driver temporarily moves the head or when an image is unclear, the head can probably be detected again near the final position of the trajectory. Therefore, when the head has become undetectable to the head detection portion 61, the head detection portion 61 searches the vicinity of the final position of the trajectory acquired by the trajectory acquisition portion 62. In this way, even when the head of the driver has become undetectable, the head may again be detected efficiently using the trajectory of the head.

The posture collapse detection portion 72 determines posture collapse of a driver during travel of the vehicle 10. When the posture has collapsed, the posture collapse detection portion 72 detects the driver is incapable of driving. Specifically, when the inclination θ of the head detected by the inclination detection portion 64 is greater than a threshold Th1 (a relative inclination threshold), the posture collapse detection portion 72 detects the driver is incapable of driving. The driving incapability state of the driver may be a case where the driver is incapable of driving.

Figure 7A:
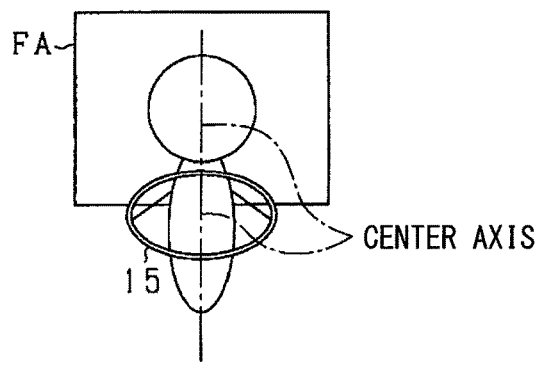
FIG. 7A is a posture during normal driving.
Figure 7B:
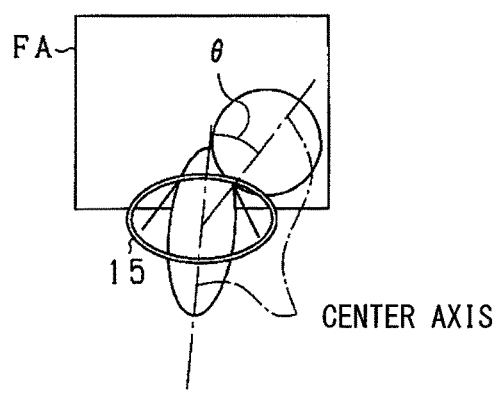
FIG. 7B is a diagram showing a posture collapse when the driver has a sudden illness.

The trunk of a driver is usually restrained by the seat 11 and seat belt 12 of the driver seat. Therefore, even when the driver has become unconscious, the trunk is less likely to move. Meanwhile, since the head of the driver is not usually restrained, the driver has to keep his or her head in position by voluntary effort. Therefore, when the driver becomes unconscious due to sudden illness, he or she cannot keep his or her head in position, and the head may significantly incline in some direction with respect to the trunk, as shown in FIGS. 7A and 7B.

Figure 8:
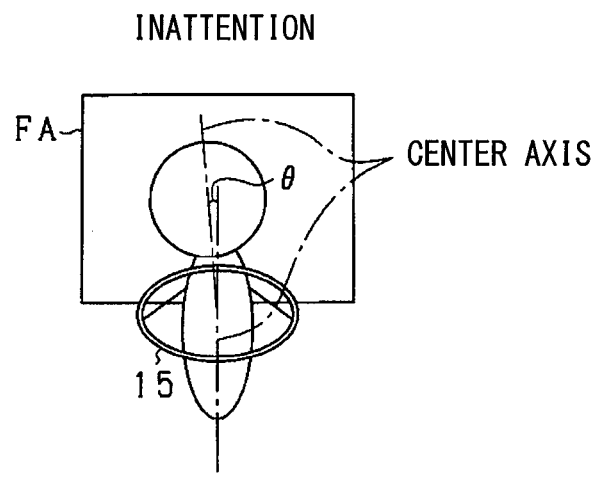
FIG. 8 is a diagram showing a posture of looking aside.
Figure 9:
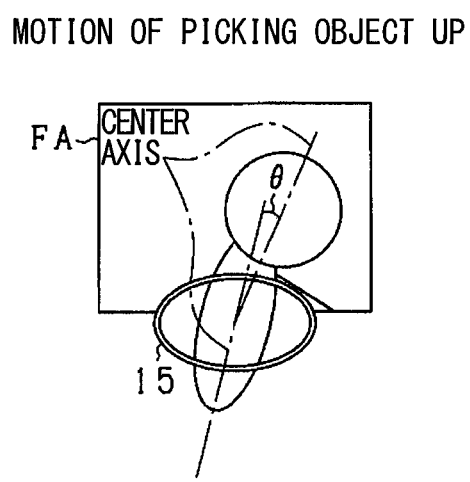
FIG. 9 is a diagram showing a posture of picking an object up.

Compared to this, when a driver looks aside during driving (drives inattentively), he or she generally sees by turning his or her head. Therefore, as shown in FIG. 8, the inclination of the head to the trunk is usually small. In addition, when the driver picks up an object located away from the driver seat, he or she generally bends his or her trunk consciously. Therefore, the inclination θ of the head to the trunk is usually small, as shown in FIG. 9. Therefore, when the inclination θ of the head is larger than a threshold Th1, the posture collapse detection portion 72 detects the driver is incapable of driving. At this time, on condition that the face of the driver is not facing in the forward direction of the vehicle 10, the posture collapse detection portion 72 detects the driver is incapable of driving, to reduce erroneous detections of the driving incapability state of a driver.

The direction collapse detection portion 73 determines collapse direction of the face of a driver during travel of the vehicle 10. When the direction of the face collapses, the direction collapse detection portion 73 detects the driver is incapable of driving. Specifically, when the direction of the face with respect to the forward direction of the vehicle 10, detected by the face direction detection portion 65, has been greater than a threshold Th2 (a face direction threshold) for longer than a time T2 (a direction collapse determination time), the direction collapse detection portion 73 detects the driver is incapable of driving.

Figure 10A:
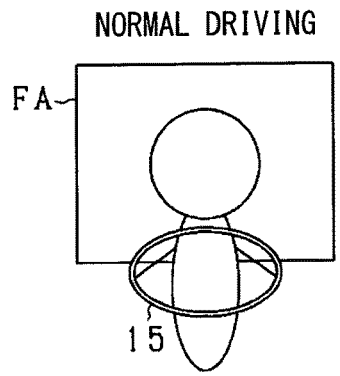
FIG. 10A is a diagram showing a face direction during normal driving.
Figure 10B:
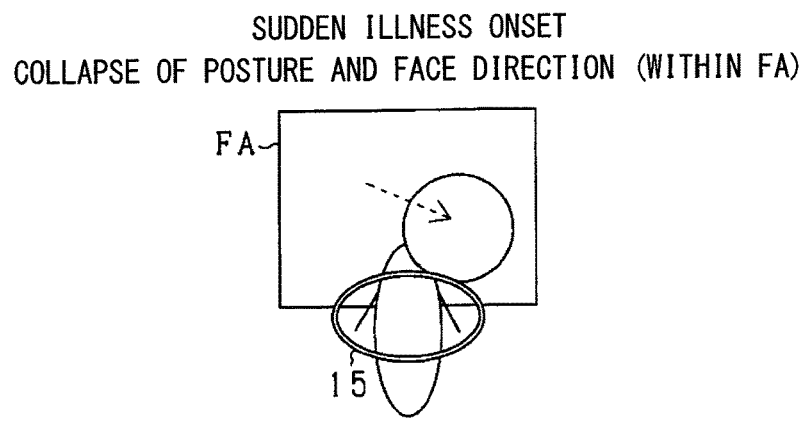
FIG. 10B is a diagram showing a direction of a face when a driver has a sudden illness.

In general, when a driver has a sudden illness, he or she cannot keep the direction of his or her face and, as shown in FIGS. 10A and 10B, the direction of the face with respect to the forward direction of the vehicle 10 remains collapsed. In comparison, when the driver looks aside during driving, the driver usually returns the direction of his or her face after changing the direction. Therefore, when the situation described above happens, the direction collapse detection portion 73 detects the driver is incapable of driving.

Alternatively, when the direction of a face with respect to the forward direction of the vehicle 10, detected by the face direction detection portion 65, is greater than the threshold Th2, and the driver is not holding the steering wheel 15, the direction collapse detection portion 73 detects the driver is incapable of driving. Whether the driver is holding the steering wheel 15 or not may be detected from an image or by a pressure sensor, or the like, installed on the steering wheel 15.

Figure 11:
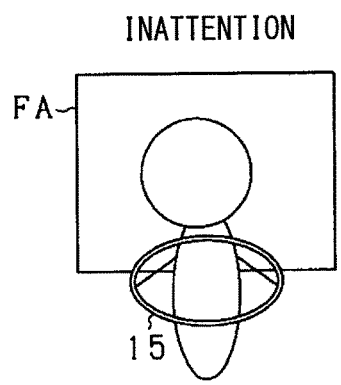
FIG. 11 is a diagram showing a direction of the face when the driver looks aside.

In general, when a driver has a sudden illness, he or she cannot keep the direction of his or her face and, as shown in FIGS. 10A and 10B, the direction of the face with respect to the forward direction of the vehicle 10 remains collapsed. In addition, the driver is usually unable to hold the steering wheel 15 any longer. Compared to this, when a driver looks aside during driving, he or she usually changes the direction of his or her face while holding the steering wheel 15, as shown in FIG. 11. Alternatively, when a driver looks aside during driving, he or she may change only the direction of his or her face by turning his or her neck without inclining his or her head. Therefore, when the situation described above happens, the direction collapse detection portion 73 detects the driver is incapable of driving.

Alternatively, when the direction of a face, detected by the face direction detection portion 65, is greater than the threshold Th2 and, in addition, opening degree of the accelerator is larger than a predetermined opening degree, the direction collapse detection portion 73 detects the driver is incapable of driving.

In general, when a driver looks aside during driving, he or she may not necessarily depress the accelerator too greatly for safety. Therefore, when the direction of his or her face with respect to the forward direction of the vehicle 10 is greater than the threshold Th2, and the opening degree of the accelerator is larger than a predetermined opening degree, there is a high possibility of collapse direction of the face resulting from his or her having a sudden illness rather than from his or her looking aside during driving and so on. Therefore, when the situation described above happens, the direction collapse detection portion 73 detects the driver is incapable of driving.

Alternatively, when the direction of a face, detected by the face direction detection portion 65, is greater than the threshold Th2 and, in addition, an accelerator operation and a brake operation are not performed for a time longer than a time T3 (operation determination time), the direction collapse detection portion 73 detects the driver is incapable of driving.

In general, when a driver has a sudden illness, the direction of his or her face with respect to the forward direction of the vehicle 10 collapses and, also, an accelerator operation and a brake operation are not performed for a time longer than the time T3. Compared to this, when a driver looks aside during driving, the driver usually changes the direction of his or her face and performs an accelerator operation or brake operation within the time T3. Therefore, when the situation described above happens, the direction collapse detection portion 73 detects the driver is incapable of driving.

The shake detection portion 74 determines shake of head of a driver, caused by external force, during travel of the vehicle 10. When the head shakes in a way different from normal, the shake detection portion 74 detects the driver is incapable of driving. Specifically, when the amplitude of shake of head detected by the head detection portion 61 is smaller than an amplitude Am1 (a first amplitude) by the time a time T5 (a shake determination time) elapses after the application of external force to the vehicle 10, or when the amplitude is larger than an amplitude Am1 (a second amplitude), the shake detection portion 74 determines the driver is incapable of driving. The amplitude Am1 is larger than the amplitude Am1.

Figure 12:
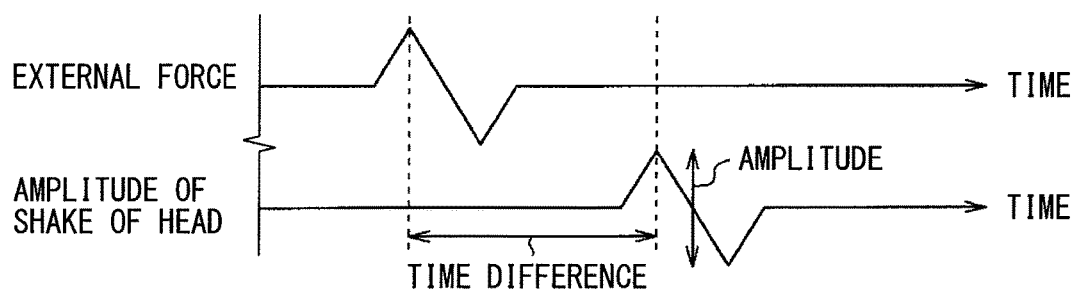
FIG. 12 is a diagram showing a shake of a head, caused by external force.
Figure 13:
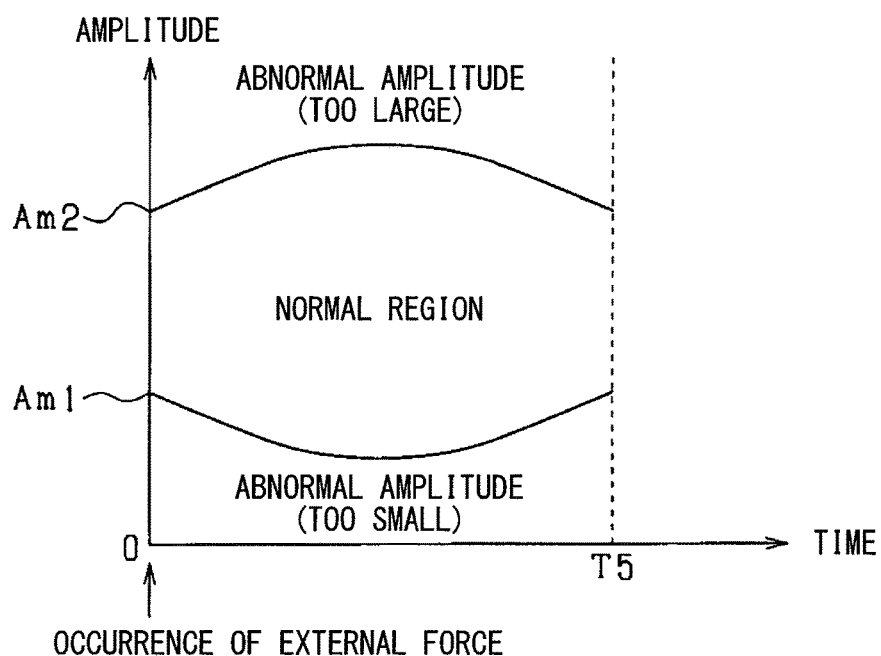
FIG. 13 is a diagram showing a range of amplitude of a shake of a head, determined as the driving incapability state.

As shown in FIG. 12, when external force is applied to the vehicle 10, vibration is transmitted to a driver after a predetermined time difference. In general, when external force (specifically, external force in a vertical direction) is applied to the vehicle 10 when the driver is conscious, the head of the driver shakes at an amplitude in a range from the amplitude Am1 to the amplitude Am1, as shown in FIG. 13. Compared to this, when a driver's body is stiff as a result of his or her having had a sudden illness, the amplitude of shake of his or her head is smaller than normal. Conversely, when a driver's body is relaxed as a result of his or her having had a sudden illness, the amplitude of shake of his or her head is larger than normal. Therefore, in a situation described above, the shake detection portion 74 detects the driving incapability state of a driver.

The time T5 is a time taken for the motion of a driver to become irrelevant to an external force after the external force has been applied to the vehicle 10. The amplitude Am1 and the amplitude Am1 are functions of time, and FIG. 13 is one example of these functions. The determination of shake may simply use, as thresholds, the minimum value of the amplitude Am1 and the maximum value of the amplitude Am1 by the time the time T5 elapses after the external force has been applied.

The white eye state detection portion 75 determines a state in which the eyes of a driver are rolled back during travel of the vehicle 10. When the state of the eyes that have been rolled back is detected by the white eye detection portion 66, the white eye state detection portion 75 detects the driver is incapable of driving. Specifically, when the exposure of the white of eye, calculated by the white eye exposure calculation portion 68, is greater than the threshold Th3 (a white eye threshold), the white eye state detection portion 75 detects the driver is incapable of driving.

Figure 14A:
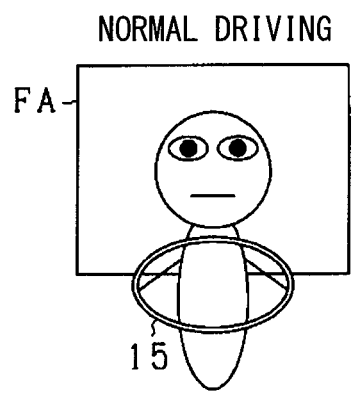
FIG. 14A is a diagram showing driver's facial expression during normal driving.
Figure 14B:
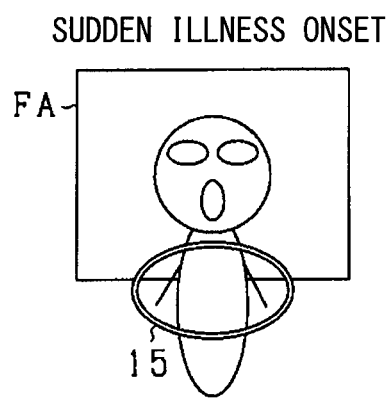
FIG. 14B is a diagram showing driver's facial expression when the driver has a sudden illness.

In general, when a driver is in the state of being able to drive, the driver's eyes do not roll back. Compared to this, when a driver has a sudden illness, the driver's eyes may be rolled back, as shown in FIGS. 14A and 14B. Therefore, when the state of eyes that have rolled back is detected, the white eye state detection portion 75 detects the driver is incapable of driving.

Each threshold and each determination value used by each state detection portion are stored in the storage device 52 (corresponding to a storage portion). In addition, the inclination θ of a head, the direction of a face, and the amplitude of shake of head, all of which have been learned by the learning portion 51, are stored in the storage device 52. Furthermore, personal information about the driver, including his or her medical history and age, is registered in the storage device 52. When there are two or more drivers, personal information about each driver is registered therein. In addition, driver's postures not to be determined as indicating driving incapability state and driver's postures determined to be indicating driving incapability state are registered in the storage device 52. Driver's postures not to be determined as indicating driving incapability state are, for example, normal driving posture and other postures often taken during driving. Driver's postures determined to be as indicating driving incapability state are, for example, postures taken when a driver, who has chronic disease, suffers a sudden attack of this disease. Using the driver cameras 21, a driver records images in advance of his or her postures in the driver seat, which he or she requests to register. He or she then registers the postures in the storage device 52.

Figure 16A:
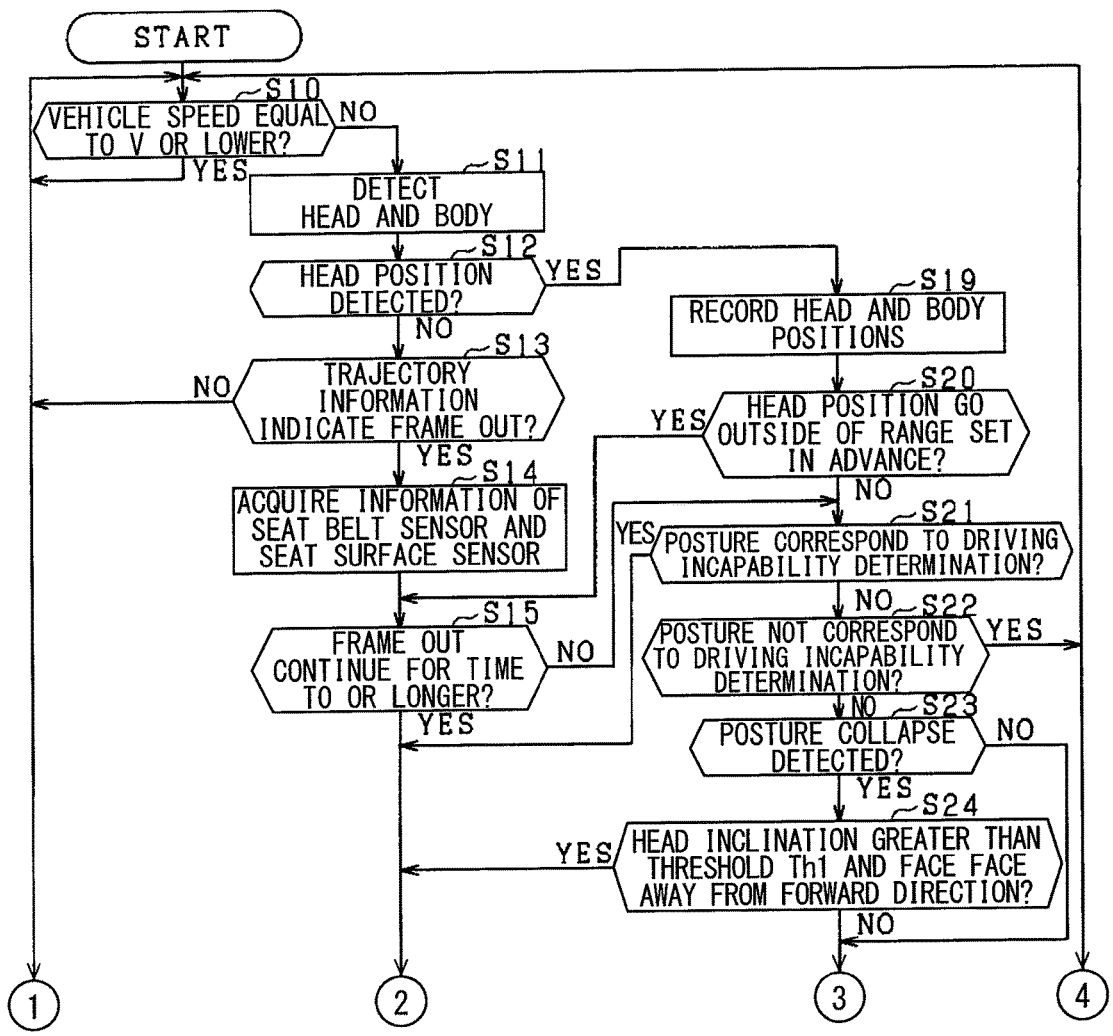
FIG. 16A is a flowchart showing a processing procedure for detecting the driving incapability state.
Figure 16B:
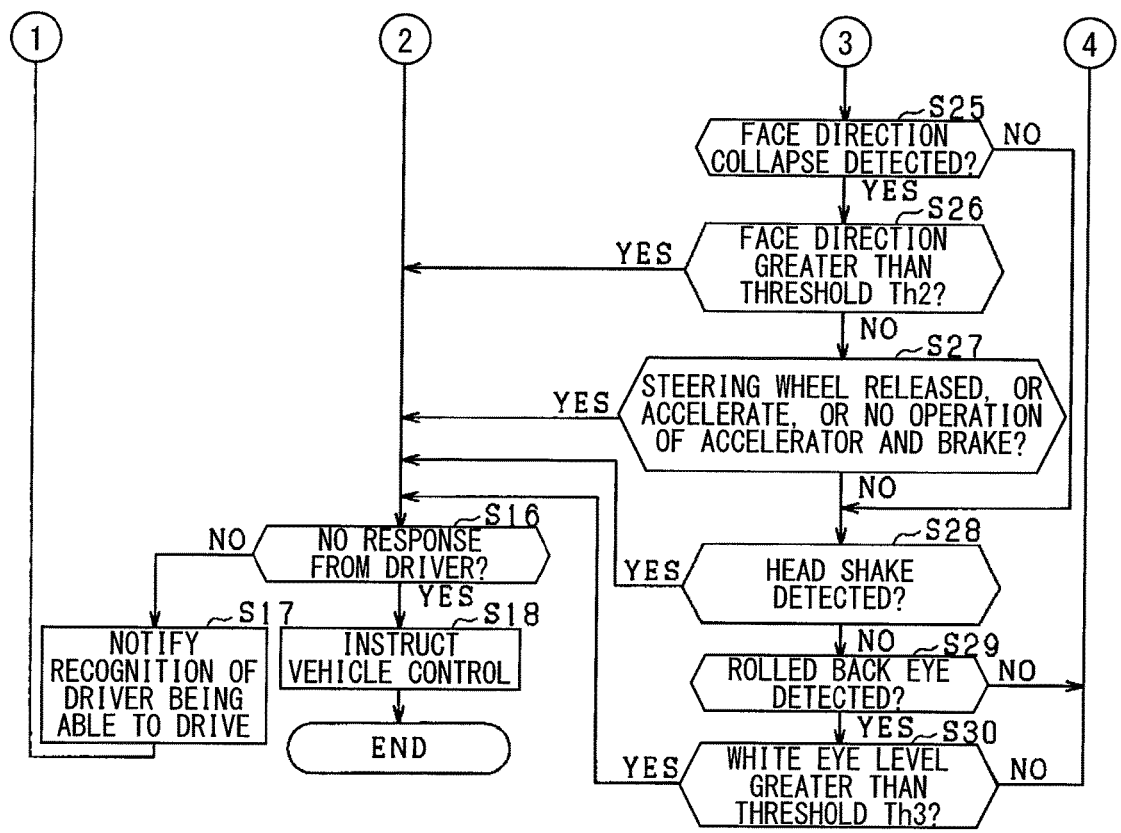
FIG. 16B is a flowchart continuing from that in FIG. 16A and showing a processing procedure for detecting the driving incapability state.

Next, processing procedure for detecting driving incapability state of a driver will be described with reference to the flowcharts in FIGS. 16A and 16B. The processing procedure is executed by the controller 50.

First, it is determined whether the vehicle speed of the vehicle 10 is equal to or lower than V (S10). The value, V, may be 0 km/h (stationary) or a sufficiently low speed as to be regarded as stationary (for example, 1 km/h). When the vehicle speed is equal to or lower than V (S10: YES), the determination in S10 is repeated until the vehicle speed is determined to be higher than V. When the vehicle speed is higher than V, (S10: NO), it is determined that the vehicle is traveling, and the process of detecting driving incapability state of a driver is initiated, and an out-of-frame determination is first made.

In the determination in S10, a determination may also be made whether a driver is performing a driving operation or not. When the driver is performing a driving operation, the determination in S10 may be repeated. When the vehicle is traveling and the driver is not performing a driving operation, the process of detecting driving incapability state of a driver may be initiated. For example, it is determined whether the vehicle speed of the vehicle 10 is equal to or higher than V2 (for example, 50 km/h), whether the steering angle detected by the steering angle sensor 32 is equal to or larger than a predetermined angle, or whether a steering angular velocity is equal to or higher than a predetermined angular velocity. The value, V2, is a value regarded such that a driver is operating an accelerator pedal; and the predetermined angle and the predetermined angular velocity are values regarded such that the driver is operating the steering wheel. When at least one of the three conditions is satisfied, it is determined that the driver is performing a driving operation, and the process of detecting driving incapability state of a driver is not initiated.

In the out-of-frame determination, the head and trunk of a driver are first detected from an image of the driver seat (S11). At this time, driver authentication is performed by detecting the features of the face included in the head of the driver. Driver authentication may be performed in advance by communication with a portable terminal such as a smart phone or by communication with the key of the vehicle 10, in which personal information has been registered.

Next, it is determined whether the position of the head could be detected or not (S12). When the position of the head could not be detected (S12: NO), trajectory information about the head is obtained from the position of the head, which has been recorded in a process S19 (described below), and then it is determined whether the trajectory information indicates the out of frame or not (S13). That is, it is determined whether non-detection of the position of the head results from the head's falling outside of an imaging range or from unclear imaging or the like.

When the trajectory information about the head does not indicate the out of frame (S13: NO), it is determined that non-detection results from temporary unclear imaging or the like and the flow returns to the processing in S10. Conversely, when the trajectory information about the head indicates the out of frame (S13: YES), it is determined that the head has fallen outside of the imaging range. At this time, information is obtained (S14) from the seat belt sensor 22 and the seat surface sensor 23 used supplementarily in order to confirm that the head is indeed present, but outside of the imaging range.

Next, it is determined whether the state of the out of frame has been continuing for the time T0 (an out-of-frame determination time) or longer (S15). Specifically, it is determined: whether the head position has been outside of the range FA for the time T0 or longer; whether the amount that the seat belt 12 has been taken-up exceeds the first amount that the seat belt 12 had been taken-up when the seat belt 12 is fastened; and whether a high-pressure portion in the pressure distribution of the seat portion 11a concentrates on the edge of the seat portion 11a. When the three conditions described above are satisfied, it is determined that the state of the out of frame has been occurring for longer than the time T0. At this time the following condition may be added: the amount that the seat belt has been taken-up per time detected by the seat belt sensor 22, that is, the rate at which the seat belt 12 has been taken-up, is larger than the second amount.

It is noted that the use of information from the seat belt sensor 22 and the seat surface sensor 23 is not indispensable. That is, the processing in S14 may be omitted, and, in the processing in S15, a determination may simply be made whether the head position is out of the range FA for a time longer than the time T0.

The time T0 is set based on personal information registered in the storage device 52. For example, the higher the age is, the shorter the time T0 is. In addition, a driver who has a specific disease is shorter in time T0 than a driver who has no disease. In addition, the time T0 is altered according to the condition of driver and traveling environment. In a case where a driver shows a sign of driving incapability state, in a case where the possibility of the driving incapability state of a driver is high, or in a traveling environment where the possibility of collision is high in the event of the driving incapability state of a driver, the time T0 is shortened to make it easier to detect the driving incapability state of a driver.

Specifically, when the head position recorded in the processing in S19 shakes at an amplitude larger than a predetermined amplitude, that is, when the head is shaking, the possibility of driving incapability state is high. Therefore, the time T0 is shortened. The higher the rate at which the head moves, the higher the possibility of posture collapse due to a sudden illness than that of posture collapse due to picking an object up. Therefore, in the obtained trajectory information about the head, the higher the rate at which the head moves, the shorter the time T0 is. In a case of posture collapse due to a sudden illness, there is a higher possibility that the closer to the edge of the range FA the head approaches, the higher the rate at which the head moves. Therefore, in a situation where the closer to the edge of the range FA the head approaches, the higher the rate at which the head moves, the possibility of posture collapse due to a sudden illness is higher than that of posture collapse due to picking an object up. Therefore, the closer to the edge of the range FA the recorded head position approaches, the higher the rate at which the head moves, and the time T0 is shortened. When spasm is detected, the possibility of driving incapability state is high and, therefore, the time T0 is shortened.

In order to avoid collision, the higher the vehicle speed is, the sooner appropriate vehicle control has to be started. Accordingly, the higher the vehicle speed of the vehicle 10 is, the shorter the time T0 is set. In order to avoid collision, the shorter the TTC (Time To Collision), obtained by dividing the vehicle distance from the preceding vehicle by the speed relative to the preceding vehicle, the sooner the appropriate vehicle control has to be started. Accordingly, the shorter the TTC is, the shorter the time T0 is set. When drive assist control such as ACC (Adaptive Cruise Control) and/or LKA (Lane Keep Assist) has been performed in the vehicle 10, a driver is likely to have posture collapse for a long time. Therefore, the time T0 is prolonged. Furthermore, on a day or in a time zone where a sudden illness such as heart attack is statistically more likely to occur, the time T0 may be shortened.

When the state of the out of frame does not exceed the time T0 (S15: NO), the flow proceeds to the processing in S21. When the state of the out of frame satisfies the time T0 or longer (S15: YES), the driving incapability state of a driver is detected and the driver is asked whether he or she is unable to drive. Specifically, by means of a sound from the speaker 82, a display on the display 81, flicker of an indicator (not shown), or the like, the driver is informed of detection of the driving incapability state of a driver. Then, it is determined whether there is a response from the driver within a predetermined time (S16).

When contact of a touch display by the driver, the voice of the driver, operation of the vehicle 10 such as the steering wheel 15 or brake, operation of a specific switch, or the like, is detected in a predetermined time, it is determined that there has been a response from the driver (S16: NO). When none of these has been detected, it is determined that there has been no response from the driver (S16: YES).

When it is determined that there has been a response from the driver, recognition that the driver is able to drive is announced by means of sound from the speaker 82, a display on the display 81, or the like (S17). Conversely, when it is determined that there has been no response from the driver, the vehicle controller 90 is instructed to safely stop the vehicle by performing appropriate braking and steering. In addition, in order to notify surrounding vehicles of the situation, the vehicle controller 90 is instructed to turn on the headlights and sound the horn (S18). Passenger/passengers in the vehicle 10 are also notified of the situation.

Next, when it is determined that the head position has been detected in the processing in S12 (S12: YES), the positions of the head and trunk are recorded (S19). From the position of the head recorded in each image, the trajectory information of the head may be obtained.

Subsequently, it is determined whether the head position is outside the preset range FA (S20). When the head position is outside the range FA although the head position is within the imaging range (S20: YES), the flow proceeds to the processing in S15, in which an out-of-frame determination is made.

Subsequently, based on positional relations of head and trunk, it is determined whether the driver's posture matches the driving incapability state, which has been registered in the storage device 52 in advance (S21). When the driver's posture matches the driving incapability state (S21: YES), it is detected that the driver is incapable of driving. Then, the flow proceeds to confirmation processing in S16.

When the driver's posture is not determined as the driving incapability state (S21: NO), it is determined whether the driver's posture matches a posture determined as the driving incapability state, which has been registered in the storage device 52 in advance (S22). When the driver's posture is not determined as the driving incapability state (S22: YES), the flow returns to the processing in S10. When the driver's posture is different from the posture not determined as the driving incapability state (S22: NO), a posture collapse determination is subsequently made.

Figure 17:
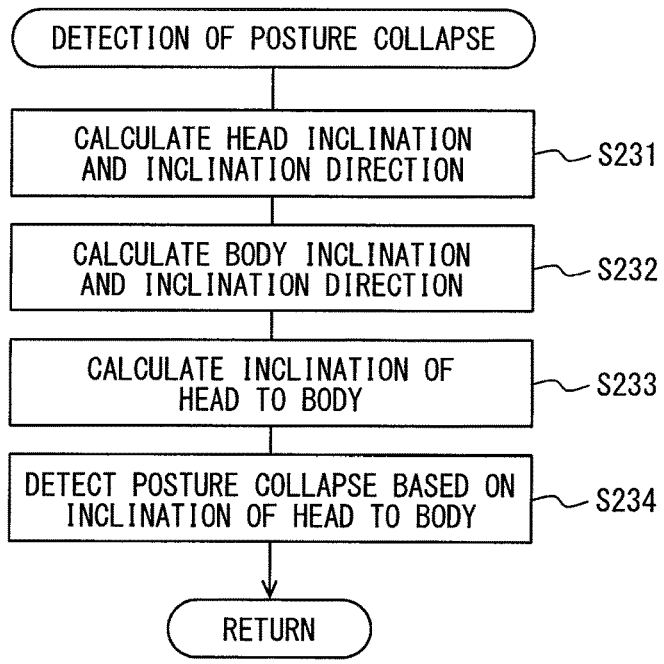
FIG. 17 shows a sub-routine showing a processing procedure for detecting a posture collapse.

First, it is determined whether a posture collapse has been detected or not (S23). Specifically, a posture collapse is detected from the process of the subroutine shown in FIG. 17. First, the inclination of the head and the direction of the inclination of the head are calculated (S231). Subsequently, the inclination of the trunk and the direction of the inclination of the trunk are calculated (S232). Next, the angle formed between the respective calculated inclinations of the trunk and head, i.e., the inclination $\theta$ of the head to the trunk, is calculated (S233). The calculated inclination $\theta$ of the head is learned when the driving incapability state of a driver is not detected. When the calculated inclination $\theta$ of the head is greater than the threshold Th1 (relative inclination value), a posture collapse is detected (S234). When a posture collapse is not detected (S23: NO), the flow proceeds to a face orientation collapse determination in S25.

When a posture collapse is detected (S23: YES), it is determined whether the inclination $\theta$ of the head has been greater than the threshold Th1 and whether the face has not been facing in the forward direction of the vehicle 10 for the time T1 or longer (S24). The time T1 corresponds to a posture collapse determination time.

At this time, the determination may use only one condition, that, for the time T1 or longer, the inclination θ of the head has been greater than the threshold Th1, or the face has not been facing in the forward direction of the vehicle 10. In addition, at this time, the determination may use the condition, that the respective calculated directions of the inclination of the head and trunk have been immobile for the time T1 or longer, that is, the respective positions of the head and trunk are within the range UA (an unmoving determination area). The range UA is the range indicating that the head and trunk have been immobile. Alternatively, the determination may use the condition, that the calculated inclination θ of the head exceeds a determination value D1 (inclination determination value) than the learned inclination of the head. Alternatively, the determination may use the condition, that the steering wheel 15 has not been operated for a time longer than a time T3 (operation determination time).

As with the time T0, the time T1 is set based on personal information registered in the storage device 52, and is altered according to vehicle speed, TTC, or the presence or absence of drive assist control. The threshold Th1 decreases when spasm is detected. Furthermore, as with the time T0, on a day or in a time zone where a sudden illness such as a heart attack is statistically more likely to occur, the time T1 may be shortened.

When the inclination θ of the head is greater than the threshold Th1 and the face has not been facing in the forward direction of the vehicle 10, for a time longer than the time T1 (S24: YES), it is detected that the driver is incapable of driving, and the flow proceeds to the confirmation processing in S16. When the inclination θ of the head has not been greater than the threshold Th1, or the face has been facing in the forward direction of the vehicle, for the time T1 or longer (S24: NO), a face direction collapse determination is subsequently made.

First, it is determined whether a face direction collapse has been detected or not (S25). Specifically, the direction of the face of the driver with respect to the forward direction of the vehicle is detected. When the detected direction of the face is greater than the threshold Th2 (face-direction threshold), a face direction collapse is detected. When a face direction collapse is not detected (S25: NO), the flow proceeds to the shake determination in S28. The detected direction of the face is learned when the driving incapability state of a driver is not detected.

When a face direction collapse is detected (S25: YES), it is determined whether the direction of the face has been greater than the threshold Th2 for the time T2 (direction collapse determination time) or longer (S26).

As with the time T0, the time T2 is set based on personal information registered in the storage device 52, and is altered according to vehicle speed, TTC, or the presence or absence of drive assist control. Furthermore, as with the time T0, on a day or in a time zone where sudden illness such as heart attack is statistically more likely to occur, the time T2 may be shortened. The threshold Th2 decreases when spasm is detected.

When the driver's face direction is greater than the threshold value Th2 for the time T2 or longer (S26: YES), it is detected that the driver is incapable of driving. Then, the flow proceeds to the confirmation processing in S16.

When the face direction has not been greater than the threshold Th2 for the time T2 or longer (S26: NO), it is determined whether, for the time T3 or longer, the driver has not been holding the steering wheel 15, opening degree of the accelerator has been greater than predetermined opening, or an accelerator operation or brake operation has not been performed (S27). When at least one of the three conditions in the processing in S27 is satisfied (S27: YES), the driving incapability state of the driver is detected, and the flow proceeds to the confirmation processing in S16. When none of the three conditions in S27 is satisfied (S27: NO), the shake determination is subsequently made.

Here, the determination in S26 may use the condition that at least one of the three conditions in S27 is satisfied. The determinations in S26 and S27 may additionally use the condition that the detected face direction exceeds the determination value D1 (inclination determination value) from the learned face direction. In general, the driving incapability state of a driver would not occur with the driver's hands being higher than his or her neck. Therefore, the condition that the driver's hands are lower than his or her neck may be used.

Next, in the shake determination, it is determined whether head shake different from normal with respect to external force has been detected (S28). Specifically, it is determined whether the amplitude of head shake has been smaller than the amplitude Am1 (first amplitude) or larger than the amplitude Am2 (second amplitude) by the time the time T5 (the shake determination time) elapses after external force has been applied to the vehicle 10.

At this time, the determination may use the condition that the head shakes at amplitude different from normal by the time the time T5 elapses after external force has been applied to the vehicle 10, and the position of the head falls within the range UA after the time T5 has elapsed. That is, the determination may use the condition that the head shakes according to external force and, after influence of external force has ceased, the position of the head does not change. Alternatively, the determination may use the condition that, when the driving incapability state of the driver is not detected, the amplitude of the head shake is learned, and the detected amplitude of the head shake is larger than the learned amplitude of the head shake by exceeding a determination value D2 (amplitude determination value). Alternatively, the determination may use the condition that the steering wheel 15 has not been operated for the time T3 or longer.

When head shakes different from normal with respect to external force has been detected (S28: YES), the driving incapability state of a driver is detected. Then, the flow proceeds to the confirmation processing in S16. When head shakes different from normal with respect to external force has not been detected (S28: NO), a white eye exposure determination is subsequently made.

First, it is determined whether a state in which driver's eyes are rolled back has been detected or not (S29). Specifically, when the calculated exposure of the white of eye is greater than the threshold Th3 (white eye threshold), it is determined that the state in which the driver's eyes are rolled back has been detected. Here, exposure of the white of each of the eyes of the driver is calculated; and on condition that exposure in each eye is greater than the threshold Th3, it is determined that the state in which the driver's eyes are rolled back has been detected. When only exposure of the white has been detected in only one eye, or when a state in which eyes are rolled back is easily detected, detection of the state in which eyes are rolled back may be determined using exposure of only the white of one eye.

When it is determined that the state in which driver's eyes are rolled back has not been detected (S29: NO), the flow returns to processing in S10 because the driving incapability state of a driver has been not detected in all the following determinations: the out-of-frame determination, the posture collapse determination, the face direction collapse determination, the shake determination, and the white eye exposure determination.

When it is determined that the state in which the driver's eyes are rolled back has been detected (S29: YES), it is determined whether exposure of the white of each eye has been greater than the threshold Th3 for the time T4 (white eye determination time) or longer (S30). At this time, the determination may additionally use the condition that the steering wheel 15 has not been operated for the time T3 or longer.

As with the time T0, the time T4 is set based on personal information registered in the storage device 52, and is altered according to vehicle speed and TTC. The threshold Th3 decreases when spasm is detected. Furthermore, as with the time T0, on a day or in a time zone where a sudden illness such as a heart attack is statistically more likely to occur, the time T4 may be shortened.

When exposure of the white of each eye has not been greater than the threshold Th3 for the time T4 or longer (S30: NO), the flow returns to processing in S10. When exposure of the white of each eye has been greater than the threshold Th3 for the time T4 or longer (S30: YES), the driving incapability state of a driver is detected. Then, the flow proceeds to the confirmation processing in S16. This is the end of the process.

Figure 18:
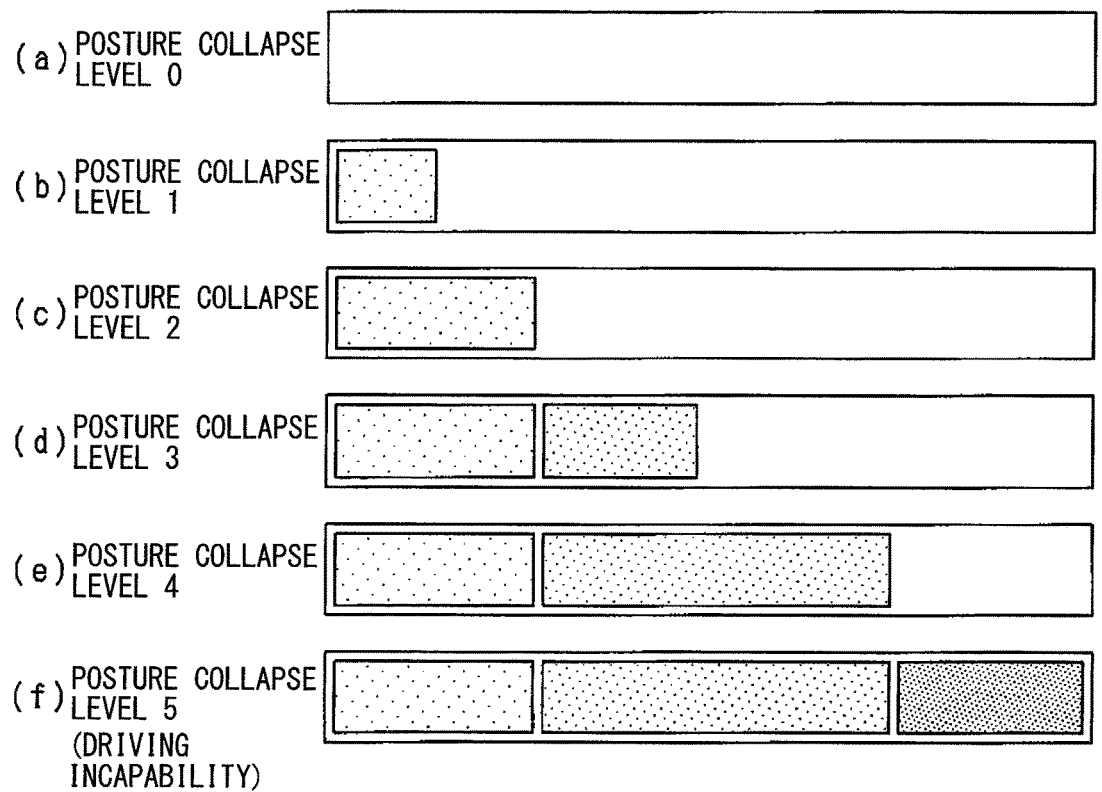
FIG. 18 is a diagram showing an aspect of notifying a driver of the level of posture collapse.

As shown in FIG. 18, the degree of posture collapse of a driver is shown on the display 81 based on the detected inclination θ of the head with respect to the trunk, the detected direction of the face, and the detected position of the head. The larger the detected inclination θ of the head, the higher the level of posture collapse set. The larger the detected direction of the face, the higher the level of posture collapse set. The farther detected position of the head is away from a standard position during driving, the higher the level of posture collapse set. The standard position during driving is the position of the head when the vehicle 10 is started, or the standard position during driving is the typical position of the head when the driving incapability state of a driver is not detected.

According to the embodiment described above, the advantageous effects described below have been yielded.

When the head of a driver falls outside the range FA, the driving incapability state of a driver is detected. Accordingly, the driving incapability state of a driver is easily detected. In addition, by taking account of trajectory obtained by the time the head falls outside the range FA, accuracy in detecting driving incapability state of a driver can be improved.

When a driver picks an object up away from the driver seat, the driver's head returns to within the range FA even when the head is temporarily away outside the range FA. Therefore, using the condition that the driver's head has been outside the range FA for a time longer than the time T0, erroneous detection of the driving incapability state of a driver can be prevented.

By covering the entire image within the range FA, the driving incapability state of a driver is detected even when the head of the driver is not present in the image. Accordingly, the detection process can be made simpler.

When the driver's posture collapses due to a sudden illness, the amount that the seat belt 12 is taken-up is more likely to exceed the first amount that the seat belt 12 is taken-up when the seat belt 12 is fastened. It is found that even when the driver's head is not detected, the driver's head is present outside the imaging range when the amount that the seat belt 12 is taken-up exceeds the first amount that the seat belt 12 is taken up when the seat belt 12 is fastened. Therefore, by using the condition that the amount that the seat belt 12 is taken-up exceeds the first amount that the seat belt 12 is taken-up when the seat belt 12 is fastened, the driving incapability state of a driver can be detected with high accuracy.

In the event that a driver has a sudden illness, the driver's posture is more likely to suddenly collapse than a case where he or she picks an object up. Therefore, in the event that a driver has a sudden illness, the seat belt 12 is more likely to be taken-up suddenly than a case where he or she picks an object up. Therefore, by using the condition that the amount that the seat belt 12 has been taken-up per time is larger than the second amount, the driving incapability state of a driver can be detected with high accuracy.

When the driver's posture collapses due to a sudden illness, the high-pressure portion in the pressure distribution of the seat portion 11a in the driver seat is more likely to concentrate on the edge of the seat portion 11a. It is found that even when the driver's head is not detected, the driver's head is present outside the imaging range when the high-pressure portion in the pressure distribution of the seat portion 11a in the driver seat concentrates on the edge of the seat portion. Therefore, by using the condition that the high-pressure portion in the pressure distribution of the seat portion 11a concentrates on the edge of the seat portion 11a, the driving incapability state of a driver can be detected with high accuracy.

A time required for determining the driving incapability state of a driver can be shortened by shortening the time T0 when the amplitude of a head shake larger than a predetermined amplitude has been detected, that is, when the head has been shaking. Hence, vehicle control can be initiated quickly when the driving incapability state of a driver is detected.

Time required to determine the driving incapability state of a driver can be shortened by making the time T0 shorter as the rate at which driver's head moves increases.

When the rate at which a head moves increases as the head approaches closer to the edge of the range FA, time required to determine the driving incapability state of a driver is made shorter. Accordingly, time required to determine the driving incapability state of a driver can be shortened.

When the inclination θ of the head to the trunk is greater than the threshold Th1, there is a high possibility of posture collapse resulting from his or her having a sudden illness rather than from his or her picking an object up. Therefore, when the inclination θ of the head to the trunk is greater than the threshold Th1, the driving incapability state of a driver is detected. Accordingly, it is possible to detect the driving incapability state of a driver with high accuracy.

When a driver consciously inclines his or her head with respect to his or her trunk greatly during travel, the driver is more likely to keep his or her face facing in the forward direction of the vehicle 10 for the purpose of safety. Therefore, by using the condition that the driver's face is not facing in the forward direction of the vehicle 10, erroneous detection of the driving incapability state of a driver can be reduced.

When a driver consciously inclines his or her head with respect to his or her trunk greatly during travel, the driver is more likely to return his or her head to initial position soon for the purpose of safety. Therefore, by using the condition that the driver's head inclines to the trunk greatly for a time longer than the time T1, erroneous detection of the driving incapability state of a driver can be reduced.

Therefore, by using the condition that the positions of the driver's head and trunk do not change for a time longer than the time T1 while the driver's head remains inclined greatly to the trunk, erroneous detection of the driving incapability state of a driver can be reduced.

By using condition that the detected inclination θ of the driver's head exceeds the learned inclination of the head by exceeding the determination value D1, erroneous detection of the driving incapability state of a driver can be reduced even when the driver has an habitual posture of bending his or her head to his or her trunk.

When the direction of the driver's face with respect to the forward direction of the vehicle 10 is greater than the threshold Th2 for a time longer than the time T2, there is a high possibility of collapse direction of the face resulting from his or her having a sudden illness rather than from his or her looking aside during driving. Therefore, by detecting driving incapability state of a driver in the foregoing situation, the driving incapability state of a driver can be detected with high accuracy.

Therefore, when the direction of the driver's face with respect to the forward direction of the vehicle 10 is greater than the threshold Th2, and the driver is not holding the steering wheel 15, there is a high possibility of collapse direction of the face resulting from his or her having a sudden illness rather than from his or her looking aside during driving. Therefore, by detecting the driving incapability state of a driver in the foregoing situation, the driving incapability state of a driver can be detected with high accuracy.

When the direction of his or her face with respect to the forward direction of the vehicle 10 is greater than the threshold Th2, and the opening degree of the accelerator is larger than a predetermined opening degree, there is a high possibility of collapse direction of the face resulting from his or her having a sudden illness rather than from his or her looking aside during driving. Therefore, by detecting the driving incapability state of a driver in the foregoing situation, the driving incapability state of a driver can be detected with high accuracy.

When the direction of his or her face with respect to the forward direction of the vehicle 10 is greater than the threshold Th2, and an accelerator operation and a brake operation are not performed for a time longer than the time T3, there is a high possibility of collapse direction of the face resulting from his or her having a sudden illness rather than from his or her looking aside during driving. Therefore, by detecting the driving incapability state of a driver in the foregoing situation, the driving incapability state of a driver can be detected with high accuracy.

In general, when a driver is in the state of being able to drive, a steering wheel operation is performed within the time T3. Therefore, by using the condition that a steering wheel operation has not been performed for a time longer than the time T3, erroneous detection of the driving incapability state of a driver can be reduced.

In general, when a driver is in the state of being able to drive, he or she does not continuously depress an accelerator greatly for a time longer than the time T3. Therefore, by using the condition that the opening degree of the accelerator is larger than a predetermined opening degree for a time longer than the time T3, erroneous detection of the driving incapability state of a driver can be reduced.

When a driver consciously changes the direction of his or her face with respect to the forward direction of the vehicle 10, he or she returns the direction of his or her face to the front soon for safety. Therefore, by using the condition that the direction of the driver's face with respect to the front of the vehicle 10 has been greater than the threshold Th2 for a time longer than the time T2, erroneous detection of the driving incapability state of a driver can be reduced.

In general, in the event that a driver has a sudden illness, the driving incapability state of a driver would not occur with the driver's hands being higher than his or her neck. Therefore, by using the condition that the driver's hands are lower than his or her neck, erroneous detection of the driving incapability state of a driver can be reduced.

When the amplitude of shake of head is smaller than the amplitude Am1 or larger than the amplitude Am2 by the time the time T5 elapses after external force has been applied to the vehicle, the driving incapability state of a driver is detected. Accordingly, the driving incapability state of a driver can easily be detected.

In general, when a driver is unconscious, his or her head shakes according to external force. When influence of external force has ceased, the head becomes immobile. On the other hand, when the driver shakes his or her head due to his or her habit, the head shakes regardless of influence of external force. Therefore, by using the condition that the driver's head shakes according to external force, and after influence of external force has ceased, the position of the head does not change, erroneous detection of the driving incapability state of a driver can be reduced.

By using condition that the detected amplitude of shake of head is larger than the learned amplitude of shake of the head by exceeding the determination value D2, erroneous detection of the driving incapability state of a driver can be reduced even when the driver has the habit of shaking his or her head.

Therefore, by detecting the driving incapability state of a driver when a state in which the driver's eyes are rolled back is detected, the driving incapability state of a driver can be detected with high accuracy.

Based on an image, the outline and black region of each eye of a driver are detected. Based on the detected outline and black region of the eye, exposure of the white of eye is calculated. When the white eye exposure is greater than the threshold Th3, the driving incapability state of a driver is detected. Therefore, the state in which the driver's eyes are rolled back is detected with high accuracy and hence the driving incapability state of a driver can be detected with high accuracy.

In general, when a driver is in the state of being able to drive, exposure of the white of each of the eyes do not remain high even when his or her sight line goes upward and consequently the exposure of the white of each eye becomes temporarily high. Therefore, by using the condition that exposure of the white of each eye has been higher than the threshold Th3 for a time longer than the time T4, erroneous detection of the driving incapability state of a driver can be reduced.

By using the condition that exposure of the white of each eye is greater than the threshold Th3, the driving incapability state of a driver is not detected when one of the eyes is not rolled back even when the other eye is covered with eye bandage or is an artificial eye, resulting in erroneous detection of a state in which the eyes are rolled back. Accordingly, erroneous detection of the driving incapability state of a driver can be reduced.

The ratio of the length (Lw+Lb) in a vertical direction of each eye to the length Lb in a vertical direction of the black eye region has a correlation with the proportion of the white eye region to the entire eye region. Therefore, exposure of the white of each eye can be calculated from the ratio of the length (Lw+Lb) in a vertical direction of each eye to the length Lb in a vertical direction of the black eye region.

The shorter the distance Lb from the top of the outline of each eye to the lowermost part of the black eye region is, the higher the exposure of the white of eye is. Accordingly, from the distance Lb from the top of the outline of each eye to the lowermost part of the black eye region, exposure of the white of eye can be calculated.

Exposure of the white of eye can be calculated from the ratio of the area of a white eye region to the area of a black eye region.

When each eye is rolled back, the black eye region is rolled upward, resulting that apparent oblateness of the black eye region become higher. Therefore, from the oblateness of the black eye region, exposure of the white of each eye can be calculated.

The longer the distance Lc from the center line in the vertical direction of the entire eye to the lowermost part of the black eye region is, the smaller the black region, and the higher the exposure of the white of eye is. Accordingly, from the distance Lc from the center line to the lowermost part of the black eye region, exposure of the white of eye can be calculated.

In general, when a driver has a spasm, the possibility of the driving incapability state is higher than that when the driver does not have a spasm. Therefore, when spasm is detected, the thresholds Th1, Th2 are decreased, thus making it easier to detect the driving incapability state of a driver.

The higher the vehicle speed is, the shorter the times T0, T1, T2, and T4 are set. Therefore, the higher the vehicle speed is, the shorter a time required to determine the driving incapability state of a driver becomes. Accordingly, appropriate vehicle control can be initiated more quickly.

The shorter the TTC is, the shorter the times T0, T1, T2, and T4 are set. Therefore, the shorter the TTC is, the shorter a time required to determine the driving incapability state of a driver becomes. Accordingly, appropriate vehicle control can be initiated more quickly.

By setting the times T0, T1, T2, and T4 based on personal information about the driver, including his or her medical history and age, a time required to determine the driving incapability state of a driver can be set according to characteristics of an individual driver.

When the drive assist control is executed in the vehicle, the times T0, T1, and T2 are prolonged, thereby reducing erroneous detection of the driving incapability state of a driver.

By notifying a driver of the degree of posture collapse of the driver, he or she can recognize his or her posture. Therefore, even when the driver's driving posture collapses, the driver can correct the posture such that it is not detected as the driving incapability state of a driver. Thus, erroneous detection of the driving incapability state of a driver can be reduced.

When the driving incapability state of a driver is detected, the driver is asked when he or she is unable to drive. Accordingly, when the driving incapability state of a driver is erroneously detected, execution of vehicle control for safely stopping the vehicle can be avoided.

Another Embodiment

The driver camera 21 may be one of the four cameras mounted in the vehicle cabin. One driver camera 21 is enough.

Based on the trajectory acquired by the trajectory acquisition portion 62, the out-of-frame detection portion 71 may detect the driver is incapable of driving, that is, the driving incapability state of a driver. When a driver becomes unable to drive as a result of his or her having had a sudden illness, there is a high possibility that the driver's head moves from a driving position but does not return to the driving position. Therefore, based on the trajectory of the head, the driving incapability state of a driver can be detected.

Even when the driver's face is facing downward greatly exceeding a threshold Th2d (downward threshold) or upward greatly exceeding a threshold Th2u (upward threshold), the direction collapse detection portion 73 may detect the driving incapability state of a driver. In general, when a driver becomes unconscious as a result of his or her having had a sudden illness, driver's face is more likely to face downward greatly exceeding the threshold Th2d or to face upward greatly exceeding the threshold Th2u. Accordingly, when the direction of the driver's face is greatly in a downward direction or upward direction, the driving incapability state of a driver can be detected.

When external force is applied to the vehicle 10 during travel of the vehicle 10, and the head detected by the head detection portion 61 has been inclining in the direction of external force for a time longer than a time T6 (a return determination time), the shake detection portion 74 may detect the driving incapability state of a driver. In general, when a driver is conscious, the driver's head returns to its initial position within the time T6 even when external force (specifically, external force in a sideways or longitudinal direction) is applied to the vehicle 10 and the driver's head consequently inclines in the direction of external force. On the other hand, when a driver is unconscious as a result of his or her having had a sudden illness, resistance of the driver's head to external force decreases, and the driver's head remains inclined in the direction of external force for a time longer than the time T6. Therefore, in the situation described above, the shake detection portion 74 detects the driving incapability state of a driver.

Even when the opening degree of a mouth (specifically, opening in a vertical direction) detected by the facial expression detection portion 67 is larger than an opening determination degree, the white eye state detection portion 75 may detect the driver is incapable of driving. When the driver's eyes are rolled back as a result of his or her having had a sudden illness, his or her mouth is more likely to open. Therefore, even when the opening degree of the driver's mouth is larger than the opening determination degree, the driving incapability state of a driver may be detected.

Detection accuracy of the driving incapability state of a driver becomes the highest by performing all the following determinations: the out-of-frame determination, the posture collapse determination, the face direction collapse determination, the shake determination, and the white eye exposure determination. However, it is enough to perform at least one of them. Alternatively, any number of the above determinations may be performed in combination. In this case, it is preferable to perform, in priority order, the out-of-frame determination, the posture collapse determination, the face direction collapse determination, the shake determination, and the white eye exposure determination.

For example, in the combination of the posture collapse determination and the shake determination, when the driving incapability state of a driver had not been detected in the posture collapse determination, the shake determination is made. Accordingly, the driving incapability state of a driver can be detected with high accuracy.

Alternatively, in the combination of the face direction collapse determination and the shake determination, when the driving incapability state of a driver had not been detected in the face direction collapse determination, the shake determination is made. Accordingly, the driving incapability state of a driver can be detected with high accuracy.

Alternatively, in the combination of the shake determination and white eye exposure determination, when the driving incapability state of a driver had not been detected in the shake determination, the white eye exposure determination is made. Accordingly, the driving incapability state of a driver can be detected with high accuracy.

The learning portion 51 may learn driver's posture when the driving incapability state of a driver is erroneously detected. Specifically, when there is a response from a driver although the driving incapability state of a driver has been detected, the driver's posture may be learned. The learned posture may be regarded as a posture which is not to be used in the determination of the driving incapability state of a driver.

The statistic values for each threshold and each determination value are stored in the storage device 52, and the values may be used as initial values. The statistic values for each threshold and each determination value are statistic results from thresholds and determination values corresponding to the drivers of multiple vehicles. Alternatively, a threshold and determination value set so as to correspond to each driver may be transmitted to an information center from the vehicle 10, and the values may be processed statistically at the information center.

When there is a response from a driver after asking the driver when he or she is unable to drive, a recognition may be made that the driver is able to drive for a fixed time thereafter. The process of detecting the driving incapability state of a driver may be performed at time intervals (for example, once per hour) set by a driver.

External force applied to the vehicle 10 may be detected by any sensor, for example, the seat surface sensor 23, other than the G sensor 44.

Thus, the apparatus detecting driving incapability state of a driver includes: an inclination detection portion that detects inclination of the head of a driver with respect to the driver's body lower than his or her neck, on the basis of an image of a driver seat captured by an imaging device mounted on a vehicle; and a posture collapse detection portion that detects the driver is incapable of driving when the inclination of the head detected by the inclination detection portion is greater than a relative inclination threshold, during travel of the vehicle.

According to the apparatus detecting driving incapability state of a driver, an inclination of the head with respect to the trunk part of the driver is detected on the basis of a captured image of a driver seat. In general, the trunk of the driver is restrained by the seat and seat belt of the driver seat. Therefore, even when the driver has become unconscious, the trunk is less likely to move. By contrast, since the head of the driver is not usually restrained, the driver has to keep the head in position by voluntary effort. Therefore, when the driver becomes unconscious due to a sudden illness, the driver cannot keep the head in position, and the head may significantly incline in some direction with respect to the trunk.

On the other hand, when the driver picks up an object located away from the driver seat, the driver generally inclines the trunk consciously. Therefore, the inclination of the head to the trunk is usually small. When a driver looks aside during driving, the driver generally sees by turning his or her head, and therefore the inclination of the head to the trunk is usually small.

Thus, when the inclination of the head with respect to the trunk is greater than a relative inclination threshold, there is a high possibility of posture collapse resulting from having a sudden illness rather than from picking up an object. Accordingly, when the inclination of the head with respect to the trunk is greater than the relative inclination threshold, the driving incapability state of the driver is detected, and it is possible to detect the driving incapability state of the driver with high accuracy.

Apparatus detecting the driving incapability state of a driver includes: a face direction detection portion that detects a direction of the face of the driver with respect to a forward direction of a vehicle based on an image of a driver seat captured by an imaging device mounted on the vehicle; and a direction collapse detection portion that detects the driving incapability state of a driver when, during travel of the vehicle, the direction of the face detected by the face direction detection portion is greater than a face direction threshold for a time longer than a direction collapse determination time.

According to the apparatus detecting the driving incapability state of a driver, the direction of the face of the driver with respect to the forward direction of the vehicle is detected based on the captured image of the driver seat. In general, when a driver has a sudden illness, he or she cannot keep the direction of his or her face and the direction of the face with respect to the forward direction of the vehicle remains collapsed. Compared this, when a driver looks aside during driving, the driver usually returns the direction of his or her face after changing the direction.

When the direction of the driver's face with respect to the forward direction of the vehicle is greater than the face direction threshold for a time longer than the face direction collapse determination time, there is a high possibility of collapse direction of the face resulting from his or her having a sudden illness rather than from his or her looking aside during driving. Therefore, when the direction of the face with respect to the forward direction of the vehicle is greater than the face direction threshold for a time longer than the direction collapse determination time, the driving incapability state of a driver is detected. Accordingly, the driving incapability state of a driver can be detected with high accuracy.

Apparatus detecting the driving incapability state of a driver includes: a face direction detection portion that detects a direction of the face of the driver with respect to a forward direction of a vehicle based on an image of a driver seat captured by an imaging device mounted on the vehicle; and a direction collapse detection portion that detects the driving incapability state of a driver when, during travel of the vehicle, the direction of the face detected by the face direction detection portion is greater than a face direction threshold and the driver is not holding the steering wheel.

According to the apparatus detecting the driving incapability state of a driver, the direction of the face of the driver with respect to the forward direction of the vehicle is detected based on the captured image of a driver seat. In general, when a driver has a sudden illness, he or she cannot keep the direction of his or her face and, the direction of the face with respect to the forward direction of the vehicle collapses. In addition, the driver is usually unable to hold the steering wheel any longer. Compared to this, when a driver looks aside during driving, he or she usually changes the direction of his or her face while holding the steering wheel.

Therefore, when the direction of the driver's face with respect to the forward direction of the vehicle is greater than the face direction threshold, and the driver is not holding the steering wheel, there is a high possibility of collapse direction of the face resulting from his or her having a sudden illness rather than from his or her looking aside during driving. Therefore, when the direction of the face with respect to the forward direction of the vehicle is greater than the face direction threshold, and the driver is not holding the steering wheel, the driving incapability state of a driver is detected. Accordingly, the driving incapability state of a driver can be detected with high accuracy.

Apparatus detecting the driving incapability state of a driver includes: a face direction detection portion that detects a direction of the face of a driver with respect to a forward direction of the vehicle based on an image of a driver seat captured by an imaging device mounted on the vehicle; and a direction collapse detection portion that detects the driving incapability state of a driver when, during travel of the vehicle, the direction of the face detected by the face direction detection portion is greater than a face direction threshold and opening degree of an accelerator is greater than a predetermined degree.

According to the apparatus detecting the driving incapability state of a driver, the direction of the face of the driver with respect to the forward direction of the vehicle is detected based on the captured image of a driver seat. In general, when a driver looks aside during driving, he or she may not necessarily depress the accelerator too greatly for safety. Therefore, when the direction of his or her face with respect to the forward direction of the vehicle is greater than the predetermined threshold, and the opening degree of the accelerator is larger than a predetermined opening degree, there is a high possibility of collapse direction of the face resulting from his or her having a sudden illness rather than from his or her looking aside during driving. Therefore, when the direction of the face with respect to the forward direction of the vehicle is greater than the face direction threshold, and the opening degree of the accelerator is larger than the predetermined opening degree, the driving incapability state of a driver is detected. Accordingly, the driving incapability state of a driver can be detected with high accuracy.

Apparatus detecting the driving incapability state of a driver includes: a face direction detection portion that detects a direction of the face of a driver with respect to a forward direction of the vehicle based on an image of a driver seat captured by an imaging device mounted on the vehicle; and a direction collapse detection portion that detects the driving incapability state of a driver when, during travel of the vehicle, the direction of the face detected by the face direction detection portion is greater than a face direction threshold and an accelerator operation and a brake operation have not been performed for a time longer than an operation determination time.

According to the apparatus detecting the driving incapability state of a driver, the direction of the face of the driver with respect to the forward direction of the vehicle is detected based on the captured image of a driver seat. In general, when a driver has a sudden illness, the direction of his or her face with respect to the forward direction of the vehicle collapses and, also, an accelerator operation and a brake operation are not performed for a time longer than the operation determination time. Compared to this, when a driver looks aside during driving, the driver usually changes the direction of his or her face and performs an accelerator operation or brake operation within the operation determination time.

Therefore, when the direction of his or her face with respect to the forward direction of the vehicle is greater than the face direction threshold, and an accelerator operation and a brake operation are not performed for a time longer than the operation determination time, there is a high possibility of collapse direction of the face resulting from his or her having a sudden illness rather than from his or her looking aside during driving. Therefore, when the direction of the face with respect to the forward direction of the vehicle is greater than the face direction threshold, and an accelerator operation and a brake operation are not performed for a time longer than the operation determination time, the driving incapability state of a driver is detected. Accordingly, the driving incapability state of a driver can be detected with high accuracy.

It is noted that a flowchart or the processing of the flowchart in the present application includes multiple steps (also referred to as sections), each of which is represented, for instance, as S10. Further, each step can be divided into several sub-steps while several steps can be combined into a single step.

While various embodiments, configurations, and aspects of apparatus detecting driving incapability state of a driver have been exemplified, the embodiments, configurations, and aspects of the present disclosure are not limited to those described above. For example, embodiments, configurations, and aspects obtained from an appropriate combination of technical elements disclosed in different embodiments, configurations, and aspects are also included within the scope of the embodiments, configurations, and aspects of apparatus detecting driving incapability state of a driver.

What is claimed is:

1. An apparatus detecting driving incapability state of a driver, the apparatus comprising:
    an imaging device that is mounted on a vehicle and is configured to capture a driver's seat;
    a memory storing an inclination detection portion and a posture collapse detection portion;
    a processor executing the inclination detection portion and the posture collapse detection portion stored in the memory;
    the inclination detection portion detects inclination of a head of a driver with respect to a trunk of the driver lower than a neck, based on an image of the driver's seat captured by the imaging device; and
    the posture collapse detection portion detects the driver is incapable of driving when the inclination of the head with respect to the trunk detected by the inclination detection portion is greater than a relative inclination threshold during travel of the vehicle, causing the vehicle to be safely stopped in a case where it is determined that the driver is incapable of driving.

2. The apparatus detecting driving incapability state of the driver according to claim 1, wherein:
    the inclination detection portion detects center axes of the head and the trunk from the image, and considers inclination of a center axis of the head with respect to a center axis of the trunk as the inclination of the head.

3. The apparatus detecting driving incapability state of the driver according to claim 1, wherein:
    the inclination detection portion detects the head and a seat belt of the driver seat from the image, and detects the inclination of the head from a positional relation between the seat belt and the head.

4. The apparatus detecting driving incapability state of the driver according to claim 1, wherein:
the posture collapse detection portion detects the driver is incapable of driving on condition that a face included in the head does not face in a forward direction of the vehicle for a time longer than a posture collapse determination time.

5. The apparatus detecting driving incapability state of the driver according to claim 1, wherein:
the posture collapse detection portion detects the driver is incapable of driving on condition that the inclination of the head is greater than the relative inclination threshold for a time longer than a posture collapse determination time.

6. The apparatus detecting driving incapability state of the driver according to claim 5, wherein:
the posture collapse detection portion detects the driver is incapable of driving on condition that a position of the head and a position of the trunk are within an unmoving determination range for a time longer than the posture collapse determination time.

7. The apparatus detecting driving incapability state of the driver according to claim 5, further comprising:
a learning portion, stored on the memory and executed by the processor, that learns the inclination of the head detected by the inclination detection portion when the driver is not incapable of driving,
wherein:
the posture collapse detection portion detects the driver is incapable of driving on condition that the inclination of the head detected by the inclination detection portion is greater than an inclination determination value by exceeding the inclination of the head learned by the learning portion.

8. The apparatus detecting driving incapability state of the driver according to claim 5, wherein:
the posture collapse detection portion detects the driver is incapable of driving on condition that a steering wheel of the vehicle is not operated for a time longer than an operation determination time.

9. The apparatus detecting driving incapability state of the driver according to claim 5, further comprising:
a shake detection portion, stored on the memory and executed by the processor, that detects the driver is incapable of driving when an amplitude of a shake of the head is smaller than a first amplitude or larger than a second amplitude, which is larger than the first amplitude, by a time a shake determination time elapses after external force has been applied to the vehicle, in a case where the posture collapse detection portion does not detect the driver is incapable of driving.

10. The apparatus detecting driving incapability state of the driver according to claim 5, further comprising:
a spasm detection portion, stored on the memory and executed by the processor, that detects spasm of the driver,
wherein:
the relative inclination threshold decreases when the spasm is detected by the spasm detection portion.

11. The apparatus detecting driving incapability state of the driver according to claim 5, wherein:
as a vehicle speed of the vehicle is high, the posture collapse determination time is shortened.

12. The apparatus detecting driving incapability state of the driver according to claim 5, wherein:
as a time to collision is short, the time being obtained by dividing a vehicle distance from a preceding vehicle by a speed relative to the preceding vehicle, the posture collapse determination time is shortened.

13. The apparatus detecting driving incapability state of the driver according to claim 5, further comprising:
a storage portion in which personal information on the driver, including medical history and age, is registered, wherein:
the posture collapse determination time is set based on the personal information registered in the storage portion.

14. The apparatus detecting driving incapability state of the driver according to claim 5, wherein:
the posture collapse determination time is prolonged when a drive assist control is executed in the vehicle.

15. The apparatus detecting driving incapability state of the driver according to claim 1, further comprising:
a posture notification portion that notifies the driver of a degree of posture collapse of the driver based on the inclination of the head detected by the inclination detection portion.

16. The apparatus detecting driving incapability state of the driver according to claim 1, wherein:
the driving incapability state includes a state in which the driver has a sudden illness.

17. The apparatus detecting driving incapability state of the driver according to claim 1, further comprising:
a face direction detection portion, stored on the memory and executed by the processor, that detects a direction of the face of the driver with respect to a forward direction of the vehicle based on the image of the driver seat captured by the imaging device mounted on the vehicle; and
a direction collapse detection portion, stored on the memory and executed by the processor, that detects the driver is incapable of driving when the direction of the face detected by the face direction detection portion is greater than a face direction threshold for a time longer than a direction collapse determination time, during travel of the vehicle in a case where the posture collapse detection portion does not detect the driver is incapable of driving.

18. The apparatus detecting driving incapability state of the driver according to claim 1, further comprising:
a face direction detection portion, stored on the memory and executed by the processor, that detects a direction of the face of the driver with respect to a forward direction of the vehicle based on the image of the driver seat captured by the imaging device mounted on the vehicle; and
a direction collapse detection portion, stored on the memory and executed by the processor, that detects the driver is incapable of driving when the direction of the face detected by the face direction detection portion is greater than a face direction threshold and the driver releases a steering wheel of the vehicle, during travel of the vehicle, in a case where the posture collapse detection portion does not detect the driver is incapable of driving.

19. The apparatus detecting driving incapability state of the driver according to claim 1, further comprising:
a face direction detection portion, stored on the memory and executed by the processor, that detects a direction of the face of the driver with respect to a forward direction of the vehicle based on the image of the driver seat captured by the imaging device mounted on the vehicle; and a direction collapse detection portion, stored on the memory and executed by the processor, that detects the driver is incapable of driving when the direction of the face detected by the face direction detection portion is greater than a face direction threshold and an opening degree of an accelerator is greater than a predetermined opening degree, during travel of the vehicle, in a case where the posture collapse detection portion does not detect the driver is incapable of driving.

20. The apparatus detecting driving incapability state of the driver according to claim 1, further comprising:
a face direction detection portion, stored on the memory and executed by the processor, that detects a direction of the face of the driver with respect to a forward direction of the vehicle based on the image of the driver seat captured by the imaging device mounted on the vehicle; and
a direction collapse detection portion, stored on the memory and executed by the processor, that detects the driver is incapable of driving when the direction of the face detected by the face direction detection portion is greater than a face direction threshold and an accelerator operation and a brake operation are not performed for a time longer than an operation determination time, during travel of the vehicle, in a case where the posture collapse detection portion does not detect the driver is incapable of driving.

21. The apparatus detecting driving incapability state of the driver according to claim 18, wherein:
the direction collapse detection portion detects the driver is incapable of driving on condition that the driver releases the steering wheel for a time longer than an operation determination time.

22. The apparatus detecting driving incapability state of the driver according to claim 19, wherein:
the direction collapse detection portion detects the driver is incapable of driving on condition that the opening degree of the accelerator is larger than the predetermined opening degree for a time longer than an operation determination time.

23. The apparatus detecting driving incapability state of the driver according to claim 19, wherein:
the direction collapse detection portion detects the driver is incapable of driving on condition that the direction of the face is greater than the face direction threshold for a time longer than a direction collapse determination time.

24. The apparatus detecting driving incapability state of the driver according to claim 23, wherein:
the direction collapse detection portion detects the driver is incapable of driving when the face faces downward greatly exceeding a downward threshold or upward greatly exceeding an upward threshold.

25. The apparatus detecting driving incapability state of a driver according to claim 18, wherein:
the direction collapse detection portion detects the driver is incapable of driving on condition that a hand of the driver is lower than a neck of the driver.

26. The apparatus detecting driving incapability state of the driver according to claim 18, further comprising:

a learning portion, stored on the memory and executed by the processor, that learns the direction of the face detected by the face direction detection portion when the driver is not incapable of driving,
wherein:
the direction collapse detection portion detects the driver is incapable of driving on condition that the direction of the face detected by the face direction detection portion is greater than the direction of the face learned by the learning portion by exceeding an inclination determination value.

27. The apparatus detecting driving incapability state of the driver according to claim 1, wherein:
the inclination detection portion detects, on a basis of a neck position of the driver, the inclination of the head with respect to the trunk based on the image of the driver seat; and
the posture collapse detection portion detects the driver is incapable of driving in response to the inclination being greater than a relative inclination threshold.

28. The apparatus detecting driving incapability state of the driver according to claim 1, wherein
the inclination detection portion detects, on a basis of a neck position of the driver, an inclination angle between the head and the trunk based on the image of the driver seat, as the inclination of the head; and
the posture collapse detection portion determines that the driver is in a driving incapable state in response to a determination that the inclination angle is greater than a predetermined threshold.

29. An apparatus detecting driving incapability state of a driver of a vehicle, the apparatus comprising:
a camera configured to capture a driver's seat of the vehicle; and
a processor configured to
detect inclination of a head of the driver with respect to a trunk of the driver lower than a neck of the driver, based on an image of the driver's seat captured by the camera, and
detect the driver is incapable of driving when the detected inclination of the head with respect to the trunk is greater than a relative inclination threshold during travel of the vehicle, causing the vehicle to be safely stopped in a case where it is determined that the driver is incapable of driving.

30. A method of detecting driving incapability state of a driver of a vehicle, the method comprising:
capturing, by a camera, a driver's seat of the vehicle;
detecting, by a processor, inclination of a head of the driver with respect to a trunk of the driver lower than a neck of the driver, based on an image of the driver's seat captured by the camera; and
detecting, by the processor, the driver is incapable of driving when the detected inclination of the head with respect to the trunk is greater than a relative inclination threshold during travel of the vehicle, causing the vehicle to be safely stopped in a case where it is determined that the driver is incapable of driving.

* * * * *